(12) United States Patent
Soldin

(10) Patent No.: US 9,269,550 B2
(45) Date of Patent: Feb. 23, 2016

(54) MASS SPECTROMETRIC METHODS FOR QUANTIFYING NPY 1-36 AND NPY 3-36

(75) Inventor: Steven J. Soldin, Bethesda, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 13/811,537

(22) PCT Filed: Jul. 22, 2011

(86) PCT No.: PCT/US2011/045012
§ 371 (c)(1),
(2), (4) Date: Apr. 4, 2013

(87) PCT Pub. No.: WO2012/012719
PCT Pub. Date: Jan. 26, 2012

(65) Prior Publication Data
US 2013/0214151 A1 Aug. 22, 2013

Related U.S. Application Data

(60) Provisional application No. 61/366,580, filed on Jul. 22, 2010.

(51) Int. Cl.
*H01J 49/00* (2006.01)
*G01N 33/68* (2006.01)

(52) U.S. Cl.
CPC ........ *H01J 49/0036* (2013.01); *G01N 33/6848* (2013.01); *G01N 2333/5755* (2013.01)

(58) Field of Classification Search
CPC .......... G01N 2030/8831; G01N 27/62; G01N 30/7233; G01N 30/88; G01N 2333/5755; G01N 33/6848; H01J 49/0036
USPC ........................................................... 436/86
See application file for complete search history.

(56) References Cited

U.S. PATENT DOCUMENTS

| | | | |
|---|---|---|---|
| 4,458,149 A * | 7/1984 | Muga | 250/287 |
| 7,371,582 B2 | 5/2008 | Nahm et al. | |
| 7,501,286 B2 * | 3/2009 | Gygi | G01N 33/68 436/173 |
| 8,741,556 B2 * | 6/2014 | Mann | G01N 33/5091 435/4 |

(Continued)

OTHER PUBLICATIONS

Abid, K et al., Kinetic study of neuropeptide Y (NPY) proteolysis in blood and identification of NPY, J. Biol. Chem 284(37): 24715-24724(2009).*

(Continued)

*Primary Examiner* — Wyatt Stoffa
(74) *Attorney, Agent, or Firm* — Alan W. Steele; Foley Hoag LLP

(57) ABSTRACT

Provided are methods of detecting the presence or amount of NPY 1-36 or NPY 3-36 in a sample using mass spectrometry. Importantly, by methods of the invention, both NPY 1-36 and NPY 3-36 can be quantified simultaneously, separately, and independently in a sample that contains both peptides. The methods provide enhanced specificity, and excellent sensitivity with limits of quantitation (LOQ) of about 0.1 ng/mL, and are accomplished in less time and with less sample preparation than required in other assays for NPY. In certain embodiments, because the methods of the invention are specific for both NPY 1-36 and NPY 3-36, the methods provide a major advantage over existing immunoassays. Therefore, the methods may be used to obtain reliable concentration data in several important patient populations, such as patients with hypertension, heart disease, or cancer.

2 Claims, 20 Drawing Sheets

(56) References Cited

U.S. PATENT DOCUMENTS

| | | | |
|---|---|---|---|
| 2004/0108452 A1* | 6/2004 | Graber | G01N 33/6803 250/281 |
| 2008/0145885 A1* | 6/2008 | Bell | C07K 14/47 435/23 |
| 2009/0090856 A1 | 4/2009 | Grant et al. | |
| 2010/0086956 A1* | 4/2010 | Newman | G01N 33/493 435/15 |
| 2010/0143938 A1* | 6/2010 | Anderson | G01N 33/6848 435/7.1 |
| 2010/0173786 A1* | 7/2010 | Brun et al. | 506/4 |
| 2010/0200742 A1* | 8/2010 | Schultz et al. | 250/252.1 |
| 2010/0311097 A1* | 12/2010 | Anderson | 435/23 |
| 2011/0190145 A1* | 8/2011 | Caprioli | 506/7 |
| 2012/0009614 A1* | 1/2012 | Zhang | G01N 33/6848 435/23 |
| 2012/0156710 A1* | 6/2012 | Nakayama | G01N 33/6848 435/23 |
| 2012/0244627 A1 | 9/2012 | Soldin | |
| 2012/0245857 A1* | 9/2012 | Lee | G06F 19/00 702/22 |
| 2012/0264154 A1* | 10/2012 | Mann | G01N 33/5091 435/23 |
| 2012/0309105 A1 | 12/2012 | Soldin | |
| 2013/0040857 A1* | 2/2013 | Anderson | G01N 33/6848 506/12 |
| 2013/0090862 A1* | 4/2013 | Krokhin | G01N 30/7233 702/21 |
| 2013/0134305 A1* | 5/2013 | Schultz et al. | 250/282 |
| 2013/0193317 A1* | 8/2013 | Mirzaei | C07K 5/1016 250/252.1 |
| 2013/0267031 A1* | 10/2013 | Middleberg | 436/86 |
| 2014/0120549 A1* | 5/2014 | Anderson | G01N 33/6848 435/7.1 |

OTHER PUBLICATIONS

Abid, k., et al., Kinetic Study of Neuropeptide Y (NPY) Proteolysis in Blood and Identification of NPY 3-35 J Biol Chem, V. 284 (37) Sep. 11, 2009.*

Stocklin, R., et. al., "A Stable Isotope Dilution Assay for the In Vivo Determination of Insulin Levels in Humans by Mass Spectrometry" Diabetes, vol. 46, Jan. 1997.*

Abid, K. et al., Kinetic study of neuropeptide Y (NPY) proteolysis in blood and identification of NPY, *J. Biol. Chem.* 284(37):24715-24724 (2009).

Nilsson, C. et al., Processing of neuropeptide Y and somatostatin in human cerebrospinal fluid as monitored by radioimmunoassay and mass spectrometry, Peptides 19(7):1137-1146 (1998).

Stenfors, C. et al., Characterization of endogenous neuropeptide Y in rat hippocampus and its metabolism by nanospray mass spectrometry, J. Biol. Chem. 272(9):5747-5751 (1997).

International Search Report and Written Opinion from parent application PCT/US2011/045012 dated Mar. 19, 2012.

Lu C et al., Dipeptidyl peptidases as survival factors in Ewing sarcoma family of tumors: Implications for tumor biology and therapy. *J Biol Chem.* 286(31):27494-27505 (2011).

Stöcklin R et al., A stable isotope dilution assay for the in vivo determination of insulin levels in humans by mass spectrometry. *Diabetes.* 46:44-50 (1997).

Supplementary European Search Report and European Search Opinion from related application EP 11810463 dated Jan. 2, 2014.

* cited by examiner

Figure 1

| | Sample Name | Sample Type | File Name | Analyte Peak Area (counts) | Analyte Peak Height (c... | Analyte Concentration (ng/mL) | Standard Query | IS Peak Area (counts) | IS U Peak ak... | Calculated Concent |
|---|---|---|---|---|---|---|---|---|---|---|
| 1 | NPY 1-36 AND 3-36 BLANK | Stan | JUNE 16 08.wiff | 4.47e+001 | 1.53e+00 | 0.00 | N/A | 2.57e+00 | 3.6 | < 0 |
| 2 | NPY 1-36 AND 3-36 0.1 NG/ML | Stan | JUNE 16 08.wiff | 9.45e+002 | 1.38e+00 | 0.100 | N/A | 9.79e+00 | 2.1 | 0.0984 |
| 3 | NPY 1-36 AND 3-36 0.2 NG/ML | Stan | JUNE 16 08.wiff | 1.70e+003 | 4.37e+00 | 0.200 | N/A | 6.62e+00 | 1.4 | 0.264 |
| 4 | NPY 1-36 AND 3-36 0.5 NG/ML | Stan | JUNE 16 08.wiff | 1.48e+003 | 1.99e+00 | 0.500 | N/A | 3.45e+00 | 6.1 | 0.442 |
| 5 | NPY 1-36 AND 3-36 2 NG/ML | Stan | JUNE 16 08.wiff | 1.77e+003 | 5.73e+00 | 2.00 | N/A | 8.18e+00 | 2.7 | 2.24 |
| 6 | NPY 1-36 AND 3-36 5 NG/ML | Stan | JUNE 16 08.wiff | 2.31e+004 | 3.83e+00 | 5.00 | N/A | 5.05e+00 | 5.9 | 4.75 |
| 7 | NPY 1-36 AND 3-36 10 NG/ML | Stan | JUNE 16 08.wiff | 8.54e+003 | 1.24e+00 | 10.0 | N/A | 4.66e+00 | 9.2 | 19.0 |
| 8 | SK-N-BE 10% FBS | Unk | JUNE 16 08.wiff | 1.24e+003 | 2.71e+00 | N/A | N/A | 1.17e+00 | 1.8 | 0.352 |
| 9 | SK-N-BE SFM | Unk | JUNE 16 08.wiff | 1.63e+003 | 2.43e+00 | N/A | N/A | 2.05e+00 | 6.2 | 0.313 |
| 10 | SK-N-MC 10%FBS | Unk | JUNE 16 08.wiff | 1.70e+002 | 4.29e+00 | N/A | N/A | 5.61e+00 | 1.3 | 0.188 |
| 11 | SK-N-MC SFM | Unk | JUNE 16 08.wiff | 7.02e+002 | 1.06e+00 | N/A | N/A | 9.62e+00 | 1.4 | 0.151 |
| 12 | SKES 10%FBS | Unk | JUNE 16 08.wiff | 1.08e+003 | 2.57e+00 | N/A | N/A | 2.71e+00 | 8.8 | 0.206 |
| 13 | SKES SFM | Unk | JUNE 16 08.wiff | 5.80e+002 | 1.47e+00 | N/A | N/A | 1.97e+00 | 4.8 | 0.153 |
| 14 | CONTROL 10%FBS | Unk | JUNE 16 08.wiff | 6.59e+002 | 1.31e+00 | N/A | N/A | 5.11e+00 | 1.1 | 0.0134 |
| 15 | CONTROL SFM | Unk | JUNE 16 08.wiff | 5.58e+002 | 1.31e+00 | N/A | N/A | 4.95e+00 | 1.0 | 0.0117 |

Figure 4

| | Sample Name | Sample Type | File Name | Analyte Peak Area (counts) | Analyte Peak Height (cps) | Analyte Concentration (ng/mL) | IS Peak Area (counts) | IS Peak | Calculated Concentration |
|---|---|---|---|---|---|---|---|---|---|
| 1 | NPY 1-36 AND 3-36 BLANK | Stan | JUNE 16 08.wiff | 2.03e+002 | 8.46e+00 | 0.00 | 2.57e+08 | 3.6 | < 0 |
| 2 | NPY 1-36 AND 3-36 0.1 NG/ML | Stan | JUNE 16 08.wiff | 2.29e+003 | 3.87e+00 | 0.100 | 9.79e+08 | 2.1 | 0.178 |
| 3 | NPY 1-36 AND 3-36 0.2 NG/ML | Stan | JUNE 16 08.wiff | 2.15e+003 | 3.05e+00 | 0.200 | 6.62e+08 | 1.4 | 0.249 |
| 4 | NPY 1-36 AND 3-36 0.5 NG/ML | Stan | JUNE 16 08.wiff | 2.28e+003 | 6.32e+00 | 0.500 | 3.45e+08 | 6.1 | 0.514 |
| 5 | NPY 1-36 AND 3-36 2 NG/ML | Stan | JUNE 16 08.wiff | 1.77e+004 | 3.55e+00 | 2.00 | 8.18e+08 | 2.7 | 1.70 |
| 6 | NPY 1-36 AND 3-36 5 NG/ML | Stan | JUNE 16 08.wiff | 3.32e+004 | 3.67e+00 | 5.00 | 5.05e+08 | 5.9 | 5.16 |
| 7 | NPY 1-36 AND 3-36 10 NG/ML | Stan | JUNE 16 08.wiff | 4.09e+003 | 6.63e+00 | 10.0 | 4.66e+08 | 9.2 | 6.89 |
| 8 | SK-N-BE 10% FBS | Unk | JUNE 16 08.wiff | 5.77e+002 | 1.68e+00 | N/A | 1.17e+08 | 1.8 | 0.00383 |
| 9 | SK-N-BE SFM | Unk | JUNE 16 08.wiff | 1.25e+003 | 1.99e+00 | N/A | 2.03e+08 | 6.2 | 0.0478 |
| 10 | SK-N-MC 10% FBS | Unk | JUNE 16 08.wiff | 2.88e+002 | 5.58e+00 | N/A | 5.61e+08 | 1.3 | 0.0397 |
| 11 | SK-N-MC SFM | Unk | JUNE 16 08.wiff | 1.10e+003 | 1.51e+00 | N/A | 9.62e+08 | 1.4 | 0.0888 |
| 12 | SKES 10% FBS | Unk | JUNE 16 08.wiff | 8.98e+002 | 2.10e+00 | N/A | 2.71e+08 | 8.8 | 0.208 |
| 13 | SKES SFM | Unk | JUNE 16 08.wiff | 3.22e+002 | 1.01e+00 | N/A | 1.97e+08 | 4.8 | 0.128 |
| 14 | CONTROL 10% FBS | Unk | JUNE 16 08.wiff | 3.72e+002 | 1.09e+00 | N/A | 5.11e+08 | 1.1 | 0.0566 |
| 15 | CONTROL SFM | Unk | JUNE 16 08.wiff | 7.68e+002 | 1.81e+00 | N/A | 4.95e+08 | 1.0 | 0.0121 |

Figure 14

```
Acquisition Information:

Acquisition Method:     NPY_Agilent C18.dam
Created:                Friday March 11    2011 11: 12: 13 AM
Last Modified:          Friday March 11    2011 11: 37: 58 AM
Comment:                Agilent C18- 15 X2.0  1.8 micron
Synchronization Mode:   LC Sync
Auto-Equilibration:     Off
Acquisition Duration:   10min0sec
Number Of Scans:        968
Periods In File:        1
Acquisition Module:     Acquisition Method
Software version        Analyst 1.4.2

Period 1:
--------------
Scans in Period:        968
Relative Start Time:    0.00 msec
Experiments in Period:  1

Period 1  Experiment   1:
---------------------------
Scan Type:              MRM (MRM)
Polarity:               Positive
Scan Mode:              N/A
Ion Source:             Turbo Spray
Resolution Q1:          Unit
Resolution Q3:          Unit
Intensity Thres.:       0.00 cps
Settling Time:          0.0000 msec
MR Pause:               5.0070 msec
MCA:                    No
Step Size:              0.00 amu Q1 Mass (amu)   Q3 Mass (amu)    Dwell(msec)   Param   Start   Stop
712.80          751.20           200.00        CE      30.00   30.00

Q1 Mass (amu)   Q3 Mass (amu)    Dwell(msec)   Param   Start   Stop
714.40          752.20           200.00        CE      30.00   30.00

Q1 Mass (amu)   Q3 Mass (amu)    Dwell(msec)   Param   Start   Stop
669.60          751.10           100.00        CE      24.00   24.00

Q1 Mass (amu)   Q3 Mass (amu)    Dwell(msec)   Param   Start   Stop
671.00          753.40           100.00        CE      24.00   24.00

Parameter Table(Period 1  Experiment   1):
CUR:         20.00
GS1:         45.00
GS2:         60.00
TEM:         650.00
ihe:         ON
IS:          5500.00
CAD:         8.00
DP           120.00
EP           10.00
CXP          15.00
```

Figure 14 (continued)

```
Shimadzu LC Method Properties
Shimadzu LC system Equlibration time = 0.10 min
Shimadzu LC system Injection Volume = 300.00 ul
Shimadzu LC Method Parameters
 Pumps
 ═══
Pump A Model: LC-20AD
Pump B Model: LC-20AD
Pump C Model: LC-20AD
Pump D Model: LC-20AD
Pumping Mode: Binary Flow
Total Flow: 0.3500 mL/min.
Pump B Pct: 10.0 %
B Curve: 0
Pump C Flow: 0.4000 mL/min.
Pump D Flow: 0.0000 mL/min.
Pressure Range (Pump A/B): 0 - 4000 psi
Pressure Range (Pump C): 0 - 4000 psi
Pressure Range (Pump D): 0 - 4000 psi
 Autosampler
 ═══
Model: SIL-20AC
Rinsing Volume: 400 uL
Needle Stroke: 52 mm.
Rinsing Speed: 35 uL/sec.
Sampling Speed: 15.0 uL/sec.
Purge Time: 10.0 min.
Rinse Dip Time: 0 sec.
Rinse Mode: Before and after aspiration
Cooler Enabled: Yes
Cooler Temperature: 4 deg. C
Control Vial Needle Stroke: 52 mm
 Oven
 ═══
Model: CTO-20A
Temperature Control: Disabled
Left Valve Position (FCV-12AH): 1
Right Valve Position (FCV-12AH): 1
 System Controller
 ═══
Model: CBM-20A
Power: On
Event 1: Off
Event 2: Off
Event 3: Off
Event 4: Off
 Time Program
 ═══
 Time     Module                Events    Parameter
 3.99              Pumps      Pump B Conc.   10
 4.00              Pumps       Pump C Flow   0.4
 4.01              Pumps      Pump B Conc.   15
 4.10              Pumps       Pump C Flow   0.1
 7.00              Pumps      Pump B Conc.   72
 7.10              Pumps      Pump B Conc.   100
 8.80              Pumps      Pump B Conc.   100
 8.90              Pumps      Pump B Conc.   5
 9.90              Pumps       Pump C Flow   0.1
 9.95              Pumps       Pump C Flow   0.4
 9.98              Pumps      Pump B Conc.   5
10.00  System Controller                   Stop
Valco Valve Method Properties
Valco Valve    Diverter
```

Figure 14 (continued)

```
     Total Time (min)    Position
1    4.0     B
2    10.0    A
```

MASS SPECTROMETRIC METHODS FOR QUANTIFYING NPY 1-36 AND NPY 3-36

RELATED APPLICATIONS

This application is the U.S. national phase of International Patent Application No. PCT/US2011/045012,filed Jul. 22, 2011, which claims the benefit of priority to U.S. Provisional Patent Application Ser. No. 61/366,580, filed Jul. 22, 2010, the contents of both of which are hereby incorporated by reference.

BACKGROUND

Neuropeptide Y (NPY) is a 36-amino acid peptide neurotransmitter found in the brain and autonomic nervous system; it is the most abundant neuropeptide in serum and plasma. NPY 1-36 has been associated with a number of physiological processes in the brain, including the regulation of energy balance, memory and learning, and epilepsy. The main effect of NPY is increased food intake and decreased physical activity. NPY 1-36 is secreted by the hypothalamus, and, in addition to increasing food intake, it increases the proportion of energy stored as fat and blocks nociceptive signals to the brain. Importantly, NPY 1-36 augments the vasoconstrictor effects of noradrenergic neurons. The full peptide is, therefore, an important diagnostic in patients suffering from hypertension, stress, and cardiovascular disease, for example.

NPY 1-36 is cleaved by dipeptidyl peptidase IV (DPPIV) into NPY 3-36, a 34-amino acid peptide fragment. NPY 3-36, however, has drastically different properties than its parent peptide; it has been shown to have an important role in cancer symptomatology. Importantly, NPY 3-36 has angiogenic properties and, therefore, may play a role in various cancer pathways, including, but not limited to, the formation and growth of solid tumors, and metastasis.

Enzyme-linked immunosorbent assay (ELISA), also known as an enzyme immunoassay (EIA), has been used to detect NPY. ELISA is a biochemical technique used mainly in immunology to detect the presence of an antibody or an antigen in a sample. In simple terms, in ELISA an unknown amount of antigen is affixed to a surface, and then a specific antibody is applied over the surface so that it can bind to the antigen. This antibody is linked to an enzyme, and in the final step a substance is added that the enzyme can convert to some detectable signal.

Importantly, current immunoassays for NPY measure NPY 1-36 and NPY 3-36 simultaneously without distinguishing them. In addition, they cross-react with many other breakdown products of the two main NPYs. This result is suboptimal, as the properties of NPY 1-36 and NPY 3-36 are different.

Efficient mass spectrometric techniques for the independent quantitation of NPY 1-36 and NPY 3-36 at physiologically relevant concentrations have been likewise unavailable. While matrix-assisted laser desorption/ionization time-of-flight mass spectrometry (MALDI-MS) has been recognized as an important tool in the study of neuropeptides due to the ability directly to detect ions at a specific mass-to-charge (m/z) ratio, even in complex biological mixtures, it has thus far been limited to determining the identity of peptide fragments produced by neuropeptide-processing, -converting, and-inactivating enzymes. Nilsson, C.; et al. "Processing of Neuropeptide Y and Somatostatin in Human Cerebrospinal Fluid as Monitored by Radioimmunoassay and Mass Spectrometry," Peptides 1998, 19(7), 1137-1146. Similarly, endogenous NPY has been qualitatively identified using a combination of chromatographic techniques and nanospray mass spectrometry. Stenfors, C.; et al. "Characterization of Endogenous Neuropeptide Y in Rat Hippocampus and Its Metabolism by Nanospray Mass Spectrometry," J. Biol. Chem. 2997, 272(9), 5747-5751.

Therefore, there exists a need for an efficient mass spectrometric technique for the independent and simultaneous quantitation of NPY 1-36 and NPY 3-36 in a sample at physiologically relevant concentrations.

SUMMARY

In certain embodiments, the invention relates to a method of assaying for NPY 1-36 or a fragment of NPY 1-36, which method comprises: a) preparing a test sample, wherein the test sample comprises NPY 1-36 or a fragment of NPY 1-36; b) combining the test sample with a known quantity of a reference peptide, thereby forming a test sample comprising an internal standard; and c) determining by mass spectrometry the quantity of the NPY 1-36 or the fragment of NPY 1-36 in the test sample and the quantity of the reference peptide in the test sample, and calibrating the quantity of the NPY 1-36 or the fragment of NPY 1-36 in the test sample against the known and determined quantities of the reference peptide in the test sample.

BRIEF DESCRIPTION OF THE FIGURES

FIG. 1 depicts exemplary experimental conditions for creating a calibration curve for the detection of NPY 1-36 on an API 4000 LC/MS/MS. NPY had previously been detected in samples 8-13 by ELISA.

FIG. 4 depicts exemplary experimental conditions for creating a calibration curve for the detection of NPY 3-36 on an API 4000 LC/MS/MS. NPY had previously been detected in samples 8-13 by ELISA.

FIG. 14 depicts an exemplary acquisition method.

DETAILED DESCRIPTION

Overview

Figure 2:
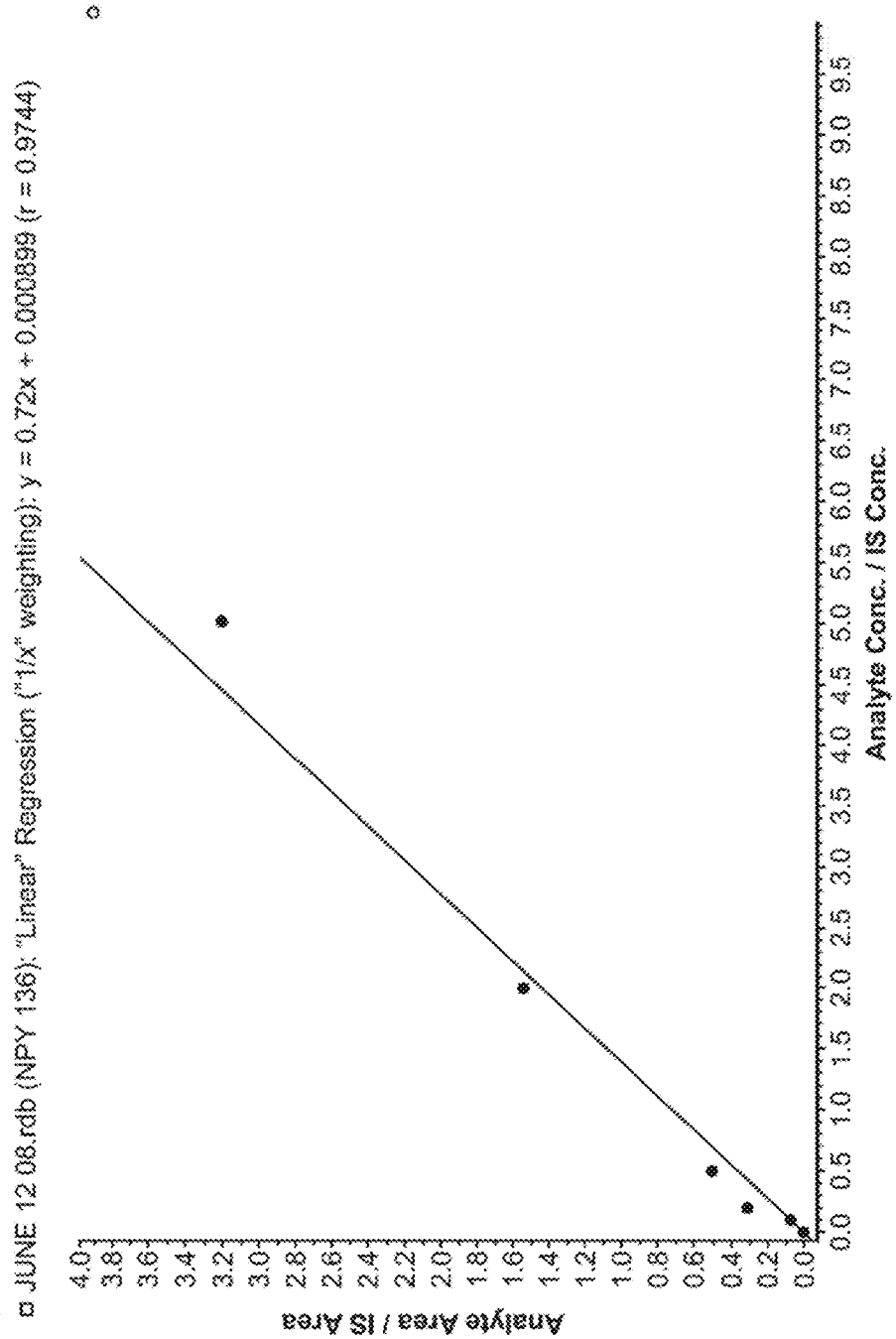
FIG. 2 depicts the calibration curve generated by samples 1 through 6 from FIG. 1. The curve displays a linear relationship up to a concentration of about 5 ng/mL of NPY 1-36.
Figure 3:
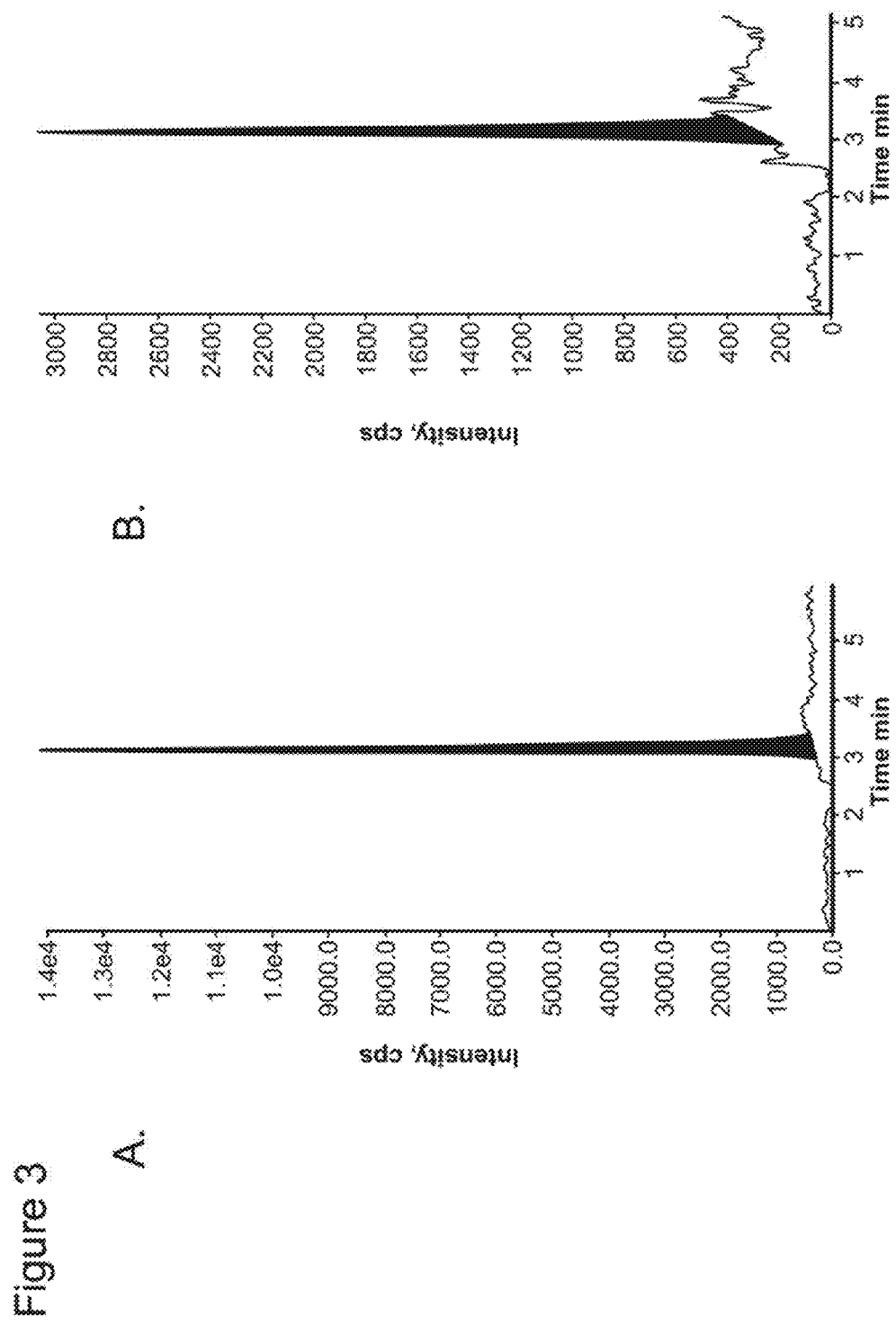
FIG. 3 depicts NPY 1-36 chromatograms, as produced on an API 4000 LC/MS/MS.

In certain embodiments, mass spectrometers may be used to provide absolute quantitation of peptides employing one or more isotopically labeled reference peptides. In certain embodiments, synthetic peptides incorporating one or more stable-isotope-labeled amino acids as a reference standard (i.e., an internal standard) may be used. In certain embodiments, such peptides may be selected based on a number of criteria, including their ionization behavior, physicochemical properties, and ease and cost of manufacture. In certain embodiments, the reference peptides are spiked into the sample of interest at a defined concentration and used as an internal standard. Because they are labeled with stable isotopes the reference peptides will have masses that are distinct from the naturally occurring forms of the peptides present in the sample of interest. In certain embodiments, the reference peptide mass will be separated by an increased mass of about 2-50 daltons compared to the natural peptide. In certain embodiments, the reference peptide mass will be separated by an increased mass of about 5-50 daltons compared to the natural peptide. In certain embodiments, the reference peptide mass will be separated by an increased mass of about 2-10 daltons compared to the natural peptide. By comparing the relative peak intensities of the natural peptide and the reference peptide, the absolute concentration of the natural peptide in the sample can be determined. In certain embodiments, the peptide to be quantitated is NPY 1-36 or NPY 3-36. In certain embodiments, the reference peptide is deuterated NPY 1-36 or deuterated NPY 3-36. In certain embodiments, the reference peptide is $D_8$-NPY 1-36 or $D_8$-NPY 3-36.

Methods are described using mass spectrometry for detecting and quantifying NPY 1-36 or NPY 3-36, or both, in a test sample. In certain embodiments, the method involves simultaneously detecting and simultaneously quantifying NPY 1-36 and NPY 3-36 in a test sample. In certain aspects, the method involves ionizing NPY 1-36 or NPY 3-36 or both in a sample comprising NPY 1-36 or NPY 3-36 or both, detecting the ion(s) by mass spectrometry, and relating the presence or amount of the ion(s) to the presence or amount of NPY 1-36 or NPY 3-36 in the sample. In certain embodiments, NPY 1-36 and NPY 3-36 can be distinguished within the same sample. In certain embodiments, either free NPY or total NPY may be determined. Certain embodiments are particularly well suited for application in large clinical laboratories. Methods of detecting and quantifying NPY 1-36 or NPY 3-36 are provided that have enhanced specificity and/or are accomplished in less time and with less sample preparation than required in other NPY assays.

Definitions

All definitions, as defined and used herein, should be understood to control over dictionary definitions, definitions in documents incorporated by reference, and/or ordinary meanings of the defined terms.

For purposes of this invention, the chemical elements are identified in accordance with the Periodic Table of the Elements, CAS version, Handbook of Chemistry and Physics, 67th Ed., 1986-87, inside cover.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "about," as used herein in reference to quantitative measurements, refers to the indicated value plus or minus 10%.

As used herein, "biological sample" refers to any sample from a biological source. As used herein, "body fluid" means any fluid that can be isolated from the body of an individual. For example, "body fluid" may include blood, plasma, serum, bile, saliva, urine, tears, perspiration, and the like.

As used herein, "derivatizing" means reacting two molecules to form a new molecule. Derivatizing agents may include Cookson-type reagents (e.g., 4-substituted 1,2,4-triazoline-3,5-diones; TAD); isothiocyanate groups, dinitrofluorophenyl groups, nitrophenoxycarbonyl groups, and/or phthalaldehyde groups. In certain embodiments, derivatization is performed using methods such as those disclosed in, for example, Vreeken, et al., Biol. Mass Spec. 22:621-632; Yeung B, et al., J. Chromatogr. 1993, 645(1):115-23; Higashi T, et al., Biol Pharm Bull. 2001, 24(7):738-43; or Higashi T, et al., J Pharm Biomed Anal. 2002, 29(5):947-55. In certain embodiments the derivatizing agents are Cookson-type reagents. Exemplary derivatizing reagents include 4-phenyl-1,2,4-triazoline-3,5-dione (PTAD); 4'-carboxyphenyl-TAD; 4-[4-(6-methoxy-2-benzoxazolyl)phenyl]-1,2,4-triazoline-3,5-dione (MBOTAD); 4-[2-(6,7-dimethoxy-4-methyl-3-oxo-3,4-dihydroquinoxalyl)ethyl]-1-1,2,4-triazoline-3,5-dione (DMEQTAD); 4-nitrophenyl-TAD; 4-pentafluorophenyl-TAD; 4-ferrocenylethyl-TAD; 4-quarternaryamine-TAD; and the like. In certain embodiments, derivatization is performed prior to chromatography; however in other embodiments derivatization is performed after chromatography, for example using methods similar to those described in Vreeken, et al., Biol. Mass Spec. 22:621-632.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

As used herein, the term "gas chromatography" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase As used herein, "mass spectrometry" (MS) refers to an analytical technique to identify compounds by their mass. MS technology generally includes (1) ionizing the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector. See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;"U.S. Pat. No. 6,124,137, entitled "Surface-Enhanced Photolabile Attachment And Release For Desorption And Detection Of Analytes;" Wright et al., Prostate Cancer and Prostatic Diseases 2:264-76 (1999); and Merchant and Weinberger, Electrophoresis 21:1164-67 (2000).

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g., ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine.

The term "field desorption" as used herein refers to methods in which a non-volatile test sample is placed on an ionization surface, and an intense electric field is used to generate analyte ions.

The term "ionization" as used herein refers to the process of generating an analyte ion having a net electrical charge equal to one or more electron units. Negative ions are those having a net negative charge of one or more electron units, while positive ions are those having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

Test Samples

Suitable test samples include any test sample that may contain the analyte of interest. In some embodiments, a sample is a biological sample; that is, a sample obtained from any biological source, such as an animal, a cell culture, an organ culture, etc. In certain embodiments, samples are obtained from a mammalian animal, such as a dog, cat, horse, etc. Exemplary mammalian animals are primates, or humans. Exemplary samples include blood, plasma, serum, cerebrospinal fluid, or other tissue sample. Such samples may be obtained, for example, from a subject; that is, a living person presenting in a clinical setting for diagnosis, prognosis, or treatment of a disease or condition. The test sample may be obtained, for example, from a subject's blood, serum, plasma, or cerebrospinal fluid.

The test sample may comprise a plurality of analytes, and in this case a calibration sample or internal standard may be provided for each analyte. In one embodiment, the analytes may be peptide fragments of a protein or polypeptide, which are produced by chemical or enzymatic processing of the protein or polypeptide. In one embodiment, the analytes may be peptides derived from the same protein or polypeptide.

In one embodiment, a plurality of test samples may be assayed for an analyte. In one embodiment, each of the plurality of test samples is assayed for the same analyte.

In certain embodiments, the term "test sample" refers to any specimen in which an analyte may be present. In certain embodiments, the test sample may comprise only one analyte. In certain embodiments, the test sample may comprise a plurality of different analytes. In certain embodiments, the test sample may be from a natural source or may be produced synthetically. In certain embodiments, an example of a synthetic sample is a mixture of recombinant proteins. In certain embodiments, the test sample is a complex mixture, for example a sample from a plant or an animal. In certain embodiments, the sample is from a human.

In certain embodiments, examples of test samples assayed in the present invention include: mammalian tissue; fluids such as blood, plasma, serum cerebrospinal fluid, synovial fluid; cell extracts, cell lines and sub-cellular organelles; tissues such as solid organ tissues, cell culture supernatants, or preparations derived from mammals, fish, birds, or insects; and tissue culture extracts.

In certain embodiments, the test sample comprises blood, serum, plasma, or cerebrospinal fluid. In certain embodiments, the test sample is blood plasma. In certain embodiments, the test sample is depleted blood plasma; that is, blood plasma which has been purified to remove the most abundant plasma proteins, such as albumin, so as to reduce the protein load in the sample, hence reducing the number of analytes in the sample.

In certain embodiments, it may be necessary to include an additive in the test sample to decrease or prevent cleavage of NPY 1-36 prior to assaying. In certain embodiments, a protease inhibitor may be added to the test sample. In certain embodiments, a peptidase inhibitor may be added to the test sample. In certain embodiments, the test sample may be added to a commercial tube charged with an inhibitor, which may be purchased for use in the present invention. In certain embodiments, the commercial tubes may be BD P100 tubes, which contain protease and peptidase inhibitors that immediately solubilize during blood collection, enhancing recovery.

Calibration Samples

In certain embodiments, the term "calibration sample" refers to a sample which comprises a known quantity of the analyte. The term "known quantity" means that the absolute quantity, or a qualitative quantity of the analyte in each aliquot of the calibration sample, is known. A qualitative quantity in the present context means a quantity which is not known absolutely, but may be a range of quantities that are expected in a subject having a particular state, for example a subject in a healthy or diseased state, or some other expected range depending on the type of test sample under investigation.

In certain methods according to the invention, the quantity of analyte in the calibration sample is a known absolute quantity. This allows for the absolute quantity of an analyte in a test sample to be determined in various methods of the invention.

In one embodiment, the same calibration sample can be used for each test sample to be assayed.

Once a reference sample is added to a test sample, the reference sample may also be referred to as an "internal standard."

In certain embodiments, the reference sample (internal standard) comprises a known quantity of the analyte, wherein the analyte of the internal standard is differentially labeled with one or more mass spectrometrically distinct groups (i.e., the analyte in the reference sample (internal standard) is a "reference peptide"), such that the analyte in the test sample can be distinguished by mass spectrometry from the internal standard. In certain embodiments, the analyte in the reference sample or internal standard, or the reference peptide, may be NPY 1-36 (IDA), human NPY 1-36, porcine NPY 1-36, isotopically labeled NPY 1-36, or isotopically labeled NPY 3-36. In certain embodiments, the reference peptide is deuterated NPY 1-36 or deuterated NPY 3-36. In certain embodiments, the reference sample (internal standard) comprises a known quantity of the analyte, wherein the analyte in the reference sample is the same as the analyte in the test sample. In certain embodiments, the reference peptides are spiked into the sample of interest at a defined concentration and used as an internal standard.

In certain embodiments, the calibration sample or internal standard may comprise a typical normal quantity of an analyte. In certain embodiments, the quantity of the analyte in the calibration sample or internal standard may indicative of a healthy animal, e.g., a human. In certain embodiments, the calibration sample or internal standard may comprise an analyte in a quantity indicative of the presence and/or stage of a particular disease. In certain embodiments, the calibration sample or internal standard comprises an analyte in a quantity indicative of the efficacy and/or toxicity of a therapy. Standard panels of known markers of a particular trait, such as presence and/or stage of disease, response to therapy, and/or toxicity, may be prepared. In certain embodiments, a known amount of an internal standard is added to multiple test samples in such a manner that, for a series of analytes, ion intensities in the MS/MS scan can be normalized based on the ion intensity of the common reference sample (internal standard), thereby providing more accurate comparisons between the separate analytes, reducing the analytical variability of the study.

Sample Preparation for Mass Spectrometry

Methods may be used prior to mass spectrometry to enrich NPY 1-36 or NPY 3-36 relative to other components in the sample, or to increase the concentration of NPY 1-36 or NPY 3-36 in the sample. Such methods include, for example, high-performance liquid chromatography (HPLC), ultrafiltration, equilibrium dialysis, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, extraction, precipitation, centrifugation, delipidization, dilution, combinations thereof and the like.

Protein precipitation is one method of preparing a liquid biological sample, such as serum or plasma. Such protein precipitation methods are well known in the art, for example, Polson et al., Journal of Chromatography B 785:263-275 (2003), describes protein precipitation methods suitable for use in the methods of the invention. In one embodiment of the invention, the protein precipitation involves adding one volume of the liquid sample (e.g., plasma) to about one to about five volumes of, for example, methanol. In another embodiment, the protein precipitation involves adding two volumes of liquid sample (e.g., plasma) to about three volumes of methanol. In certain embodiments, the use of protein precipitation obviates the need for high turbulence liquid chromatography ("HTLC") or on-line extraction prior to HPLC and mass spectrometry. In certain embodiments, trichloroacetic acid (TCA), acetone, chloroform/methanol, or ammonium sulfate may be used. In certain embodiments, ammonium sulfate fractionation can efficiently remove albumin, which typically represents more than 50% of plasma proteins.

Ultrafiltration, a variety of membrane filtration used in industry and research for purifying and concentrating macromolecular solutions, may be used to prepare the samples for mass spectrometry. In certain embodiments, ultrafiltration is used to remove high-molecular weight molecules from a sample. In certain embodiments, ultrafiltration is used to remove molecules having a molecular weight above about 30 kDa from a sample. In certain embodiments, ultrafiltration at about 37° C. (human physiological temperature) is used to remove molecules having a molecular weight above about 30 kDa from a sample. In certain embodiments, ultrafiltration may be applied in cross-flow or dead-end mode and separation in ultrafiltration undergoes concentration polarization. In certain embodiments, ultrafiltration may take place at around 37° C., approximate physiological temperature. In certain embodiments, ultrafiltration yields free NPY 1-36 or free NPY 3-36. In certain embodiments, free NPY 1-36 or free NPY 3-36 is present in a sample at a concentration less than that of total NPY 1-36 or total NPY 3-36. In certain embodiments, carrying out ultrafiltration prior to MS, while it may make the quantification process slightly less efficient, is desirable because of the ability to obtain a measurement of the free NPY product. In certain embodiments, immediately following ultrafiltration, an additive (e.g., an antioxidant or enzyme inhibitor) may be added to the sample (i.e., the filtrate). Examples of additives are described below in more detail.

Liquid Chromatography

Generally, chromatography may be performed prior to mass spectrometry; the chromatography may be liquid chromatography, such as high performance liquid chromatography (HPLC).

Liquid chromatography (LC) including high-performance liquid chromatography (HPLC) relies on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples; however, a significant amount of sample preparation is required prior to the separation and subsequent analysis with a mass spectrometer (MS), making this technique labor intensive. In addition, most HPLC systems do not utilize the mass spectrometer to its full potential, allowing only one HPLC system to be connected to a single MS instrument, resulting in substantial time requirements for performing a large number of assays.

Various methods have been described involving the use of HPLC for sample clean-up prior to mass spectrometry analysis. See, e.g., Taylor et al., Therapeutic Drug Monitoring 22:608-12 (2000) (manual precipitation of blood samples, followed by manual C18 solid phase extraction, injection into an HPLC for chromatography on a C18 analytical column, and MS/MS analysis); and Salm et al., Clin. Therapeutics 22 Supl. B:B71-B85 (2000) (manual precipitation of blood samples, followed by manual CIS solid phase extraction, injection into an HPLC for chromatography on a C18 analytical column, and MS/MS analysis).

One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, but are not limited to these groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e., mixed) mode. During chromatography, the separation of materials is effected by variables such as choice of eluent (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

Recently, high turbulence liquid chromatography ("HTLC"), also called high throughput liquid chromatography, has been applied for sample preparation prior to analysis by mass spectrometry. See, e.g., Zimmer et al., J. Chromatogr. A 854:23-35 (1999); see also, U.S. Pat. Nos. 5,968,367; 5,919,368; 5,795,469; and 5,772,874 (all four of which are incorporated by reference). Traditional HPLC analysis relies on column packings in which laminar flow of the sample through the column is the basis for separation of the analyte of interest from the sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the NPY 1-36 or fragment of NPY 1-36 prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. In certain embodiments of the method, samples are subjected to protein precipitation as described above prior to loading on the HTLC column; in alternative embodiments, the samples may be loaded directly onto the HTLC without being subjected to protein precipitation.

Detection and Quantitation by Mass Spectrometry

In certain embodiments, the invention provides useful methods for determining relative and/or absolute quantities of analytes, such as peptides. In certain embodiments, the invention relates to detection of analytes by tandem mass spectrometry, and associated methods of analyzing test samples containing a known concentration of an internal standard. In certain embodiments, relative and/or absolute quantitation of the analytes is facilitated by methods of the invention.

In certain embodiments, the invention relates to methods for assaying analytes by mass spectrometry in a variety of settings including measurement of protein changes in cells, tissues and fluids in human or veterinary sciences.

In certain embodiments, the invention relates to a method in which the quantities of the analyte and internal standard in a test sample or a calibration sample are determined by mass spectrometry. In certain embodiments, a calibration function is used to relate the quantity of the analyte in the test sample as measured by mass spectrometry to the actual quantity of the analyte in the test sample. In certain embodiments, this calibration function uses the quantities of the analyte and internal standard in a calibration sample (both the actual quantities prior to analysis and the corresponding quantities as measured by mass spectrometry) as variables.

In certain embodiments, the method comprises the step of plotting a graph of the known quantities of the analyte and internal standard in the calibration sample versus the signal obtained by the MS for the test sample. In certain embodiments, this step may instead merely involve calculation. In certain embodiments, the quantity of the analyte in the test sample may then be calculated by measuring the quantity in the test sample as determined by mass spectrometry against the calibration graph. In certain embodiments, a reference to "a quantity as measured by mass spectrometry" is typically an ion abundance, ion intensity, or other signal measured by mass spectrometry which relates to the quantity of an analyte.

Disclosed are mass spectrometric methods for detecting in a sample the presence or amount of NPY 1-36 or a NPY fragment, such as NPY 3-36. In certain aspects, the method involves ionizing NPY 1-36 or NPY 3-36 or both in a sample comprising NPY 1-36 or NPY 3-36 or both, detecting the ion(s) by mass spectrometry, and relating the presence or amount of the ion(s) to the presence or amount of NPY 1-36 or NPY 3-36 or both in the sample.

Mass spectrometry may be performed using a mass spectrometer which includes an ion source for ionizing the fractionated sample and creating charged molecules for further analysis. For example, ionization of the sample may be performed by electrospray ionization (ESI), atmospheric pressure chemical ionization (APCI), atmospheric pressure photoionization (APPI), photoionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the resulting positively charged or negatively charged ions may be analyzed to determine a mass-to-charge ratio (i.e., m/z). Suitable analyzers for determining mass-to-charge ratios include quadrupole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM). Often, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas to produce the daughter ions. Because both the precursor and fragment ions are produced in a reproducible fashion under a given set of ionization/fragmentation conditions, the MS/MS technique can provide an extremely powerful analytical tool. For example, the combination of filtration and fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in short ion pulses. Successful TOF detection and quantitation depends on choosing a method based on accurate mass which is reliable to 4 or 5 decimal places. In these instances, a single ion is monitored which may have multiple charges. Mass spectrometers that combine time-of-flight analyzers with tandem MS are well known to the skilled artisan. Additionally, multiple mass spectrometry steps can be combined in methods known as "MS/MS$_n$." Various other combinations may be employed, such as TOF, MS/MS/TOF, MALDI/MS/MS/TOF, or SELDI/MS/MS/TOF mass spectrometry.

The results of an analyte assay (i.e., a mass spectrum), can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule. In certain embodiments, an internal standard is used to generate a standard curve for calculating the quantity of NPY 1-36 or NPY 3-36. Methods of generating and using such standard curves are well known in the art and one of ordinary skill is capable of selecting an appropriate internal standard. For example, an isotope of NPY 1-36 or NPY 3-36 may be used as an internal standard. In some embodiments, NPY 1-36 or NPY 3-36 is deuterated. In certain embodiments, multiple deuterium atoms are present in the NPY 1-36 or NPY 3-36 internal standard. Numerous other methods for relating the presence or amount of an ion to the presence or amount of the original molecule will be well known to those of ordinary skill in the art.

One or more steps of the methods of the invention can be performed in an automated fashion. In certain embodiments, one or more purification steps are performed on line, and all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In certain embodiments, NPY 1-36 and NPY 3-36 are detected and/or quantified using the following procedure: The analytes (i.e., NPY 1-36 and NPY 3-36) are ionized by the corona discharge needle of the interface, which applies a large voltage to the nebulized solvent/analyte mixture. The ions, i.e., precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of the specific NPY 1-36 or NPY 3-36 to be analyzed. Precursor ions with the correct m/z ratios of the precursor ions of specific NPY 1-36 or NPY 3-36 are allowed to pass into the collision chamber (Q2), while unwanted ions with any other m/z collide with the sides of the quadrupole and are eliminated. Precursor ions entering Q2 collide with neutral argon gas molecules or nitrogen gas molecules and fragment. This process is called Collision Activated Dissociation (CAD). The fragment ions generated are passed into quadrupole 3 (Q3), where the fragment ions of the desired NPY 1-36 and NPY 3-36 are selected while other ions are eliminated.

The methods of the invention may involve MS/MS performed in either positive ion or negative ion mode. Using standard methods known in the art, one of ordinary skill is capable of identifying one or more fragment ions of a particular precursor ion of NPY 1-36 or NPY 3-36 that can be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (NPY 1-36 or NPY 3-36) of interest. In certain embodiments, the area under the curves, or amplitude of the peaks, for fragment ion(s) and/or precursor ions are measured to determine the amount of NPY 1-36 or NPY 3-36. As described above, the relative abundance of a given ion can be converted into an absolute amount of the original analyte, i.e., NPY 1-36 or NPY 3-36, using calibration standard curves based on peaks of one or more ions of an internal molecular standard.

In certain aspects of the invention, the quantity of various ions is determined by measuring the area under the curve or the amplitude of the peak and a ratio of the quantities of the ions is calculated and monitored (i.e., "daughter ion ratio monitoring"). In certain embodiments of the method, the ratio(s) of the quantity of a precursor ion and the quantity of one or more fragment ions of NPY 1-36 or NPY 3-36 can be calculated and compared to the ratio(s) of a molecular standard of NPY 1-36 or NPY 3-36 similarly measured. In embodiments where more than one fragment ion of NPY 1-36 or NPY 3-36 is monitored, the ratio(s) for different fragment ions may be determined instead of, or in addition to, the ratio of the fragment ion(s) compared to the precursor ion. In embodiments where such ratios are monitored, if there is a substantial difference in an ion ratio in the sample as compared to the molecular standard, it is likely that a molecule in the sample is interfering with the results. To the contrary, if the ion ratios in the sample and the molecular standard are similar, then there is increased confidence that there is no interference. Accordingly, monitoring such ratios in the samples and comparing the ratios to those of authentic molecular standards may be used to increase the accuracy of the method.

In certain embodiments of the invention, the presence or absence or amount of other fragments of NPY 1-36 in a sample may be detected in a single assay using the above described MS/MS methods.

Selected Methods

In certain embodiments, the invention relates to a method of assaying for NPY 1-36 or a fragment of NPY 1-36, which method comprises: a) preparing a test sample, wherein the test sample comprises NPY 1-36 or a fragment of NPY 1-36; b) combining the test sample with a known quantity of a reference peptide, thereby forming a test sample comprising an internal standard; and c) determining by mass spectrometry the quantity of the NPY 1-36 or the fragment of NPY 1-36 in the test sample and the quantity of the reference peptide in the test sample, and calibrating the quantity of the NPY 1-36 or the fragment of NPY 1-36 in the test sample against the known and determined quantities of the reference peptide in the test sample.

In certain embodiments, the invention relates to any one of the aforementioned methods, wherein the reference peptide is differentially labeled with one or more mass spectrometrically distinct groups, such that the NPY 1-36 or the fragment of NPY 1-36 and the reference peptide can be distinguished by mass spectrometry. In certain embodiments, the reference peptide is NPY 1-36 (IDA), human NPY 1-36, porcine NPY 1-36, isotopically labeled NPY 1-36, or isotopically labeled NPY 3-36. In certain embodiments, the reference peptide is deuterated NPY 1-36 or deuterated NPY 3-36.

In certain embodiments, the invention relates to any one of the aforementioned methods, wherein step (c) comprises: i) in a mass spectrometer selecting and fragmenting ions of a mass to charge ratio corresponding to the reference peptide, and detecting and producing a first mass spectrum of first fragment ions; ii) in a mass spectrometer selecting and fragmenting ions of a mass to charge ratio corresponding to the NPY 1-36 or the fragment of NPY 1-36, and detecting and producing a second mass spectrum of second fragment ions; and iii) determining the quantity of the NPY 1-36 or the fragment of NPY 1-36 in the test sample on the basis of the quantity of the second fragment ions in the second mass spectrum relative to the quantities of the first fragment ions from the reference peptide in the second mass spectrum.

In certain embodiments, the invention relates to any one of the aforementioned methods, wherein the test sample comprises both NPY 1-36 and a fragment of NPY 1-36. In certain embodiments, the invention relates to any one of the aforementioned methods, wherein the test sample comprises both NPY 1-36 and NPY 3-36.

In certain embodiments, the present invention relates to any one of the aforementioned methods, wherein the test sample comprises a biological fluid.

In certain embodiments, the present invention relates to any one of the aforementioned methods, wherein the performance of steps (a), (b), and (c) takes place in less than about six hours. In certain embodiments, the present invention relates to any one of the aforementioned methods, wherein the performance of steps (a), (b), and (c) takes place in less than about four hours. In certain embodiments, the present invention relates to any one of the aforementioned methods, wherein the performance of steps (a), (b), and (c) takes place in less than about two hours. In certain embodiments, the present invention relates to any one of the aforementioned methods, wherein the performance of steps (a), (b), and (c) takes place in less than about one hour. In certain embodiments, the present invention relates to any one of the aforementioned methods, wherein the performance of steps (a), (b), and (c) takes place in less than about 45 minutes. In certain embodiments, the present invention relates to any one of the aforementioned methods, wherein the performance of steps (a), (b), and (c) takes place in less than about 30 minutes. In certain embodiments, the present invention relates to any one of the aforementioned methods, wherein the performance of steps (a), (b), and (c) takes place in less than about 15 minutes. In certain embodiments, the present invention relates to any one of the aforementioned methods, wherein the performance of steps (a), (b), and (c) takes place in less than about 10 minutes. In certain embodiments, the present invention relates to any one of the aforementioned methods, wherein the performance of steps (a), (b), and (c) takes place in less than about 5 minutes.

In certain embodiments, the present invention relates to any one of the aforementioned methods, wherein the NPY 1-36 or the fragment of NPY 1-36 is present in the test sample at a concentration of about 1 pg/mL to about 10,000 pg/mL. In certain embodiments, the present invention relates to any one of the aforementioned methods, wherein the NPY 1-36 or the fragment of NPY 1-36 is present in the test sample at a concentration of about 10 pg/mL to about 8,000 pg/mL. In certain embodiments, the present invention relates to any one of the aforementioned methods, wherein the NPY 1-36 or the fragment of NPY 1-36 is present in the test sample at a concentration of about 100 pg/mL to about 7,000 pg/mL. In certain embodiments, the present invention relates to any one of the aforementioned methods, wherein the NPY 1-36 or the fragment of NPY 1-36 is present in the test sample at a concentration of about 100 pg/mL to about 3,000 pg/mL. In certain embodiments, the present invention relates to any one of the aforementioned methods, wherein the NPY 1-36 or the fragment of NPY 1-36 is present in the test sample at a concentration of less than about 6,000 pg/mL, less than about 5,000 pg/mL, less than about 4,000 pg/mL, less than about 3,000 pg/mL, less than about 2,000 pg/mL, less than about 1,000 pg/mL, less than about 900 pg/mL, less than about 800 pg/mL, less than about 700 pg/mL, less than about 600 pg/mL, less than about 500 pg/mL, less than about 400 pg/mL, less than about 300 pg/mL, less than about 200 pg/mL, less than about 100 pg/mL, less than about 90 pg/mL, less than about 80 pg/mL, less than about 70 pg/mL, less than about 60 pg/mL, less than about 50 pg/mL, less than about 40 pg/mL, less than about 30 pg/mL, less than about 20 pg/mL, or less than about 10 pg/mL.

In certain embodiments, the present invention relates to any one of the aforementioned methods, wherein the mass spectrometer is a Quadrupole Time-of-Flight (Q-TOF) mass spectrometer, Ion Trap Time-of-Flight (IT-TOF) mass spectrometer, Time-of-Flight (TOF) mass spectrometer or a triple QUAD mass spectrometer.

In certain embodiments, the present invention relates to any one of the aforementioned methods, wherein the fragmentation is caused by electrospray ionization (ESI), Collision Induced Dissociation (CID), Surface Induced Dissociation (SID), Electron Capture Dissociation (ECD), Electron Transfer Dissociation (ETD), or Fast Atom Bombardment.

In certain embodiments, the present invention relates to any one of the aforementioned methods, further comprising the step of separating the components of the test sample prior to step (a). In certain embodiments, this step involves ultrafiltration or protein precipitation.

In certain embodiments, the present invention relates to any one of the aforementioned methods, further comprising the step of adding an additive to the test sample. In certain embodiments, the additive is a protease inhibitor. In certain embodiments, the additive is a peptidase inhibitor. In certain embodiments, the additive is an anti-oxidant. In certain embodiments, the additive is dithiothreitol (DTT).

In certain embodiments, the present invention relates to any one of the aforementioned methods, wherein at least one of the second fragment ions has a mass/charge ratio of between about 500 and about 1800. In certain embodiments, the present invention relates to any one of the aforementioned methods, wherein at least one of the second fragment ions has a mass/charge ratio of between about 600 and about 1600. In certain embodiments, the present invention relates to any one of the aforementioned methods, wherein at least one of the second fragment ions has a mass/charge ratio of between about 1300 and about 1500. In certain embodiments, the present invention relates to any one of the aforementioned methods, wherein at least one of the second fragment ions has a mass/charge ratio of about 611, about 751, about 803, about 855, about 1343 or about 1430. In certain embodiments, the present invention relates to any one of the aforementioned methods, wherein at least one of the second fragment ions has a mass/charge ratio of about 611.4, about 751.3, about 803.20, about 855.22, about 1343.53 or about 1430.23. In certain embodiments, the present invention relates to any one of the aforementioned methods, wherein at least one of the first fragment ions has a mass/charge ratio of about 575 or about 603. In certain embodiments, the present invention relates to any one of the aforementioned methods, wherein at least one of the first fragment ions has a mass/charge ratio of about 575.3 or about 603.0.

In certain embodiments, the present invention relates to any one of the aforementioned methods, wherein at least one of the first fragment ions or second fragment ions results from the loss of water from a parent ion. In certain embodiments, the present invention relates to any one of the aforementioned methods, wherein at least one of the first fragment ions or second fragment ions results from the loss of one water molecule from a parent ion. In certain embodiments, the present invention relates to any one of the aforementioned methods, wherein at least one of the first fragment ions or second fragment ions results from the loss of two water molecules from a parent ion. In certain embodiments, the present invention relates to any one of the aforementioned methods, wherein at least one of the first fragment ions or second fragment ions results from the loss of three water molecules from a parent ion.

In certain embodiments, the present invention relates to any one of the aforementioned methods, wherein the NPY 1-36 or fragment of NPY 1-36 in the test sample is free NPY 1-36 or free fragment of NPY 1-36. In certain embodiments, the present invention relates to any one of the aforementioned methods, wherein the NPY 1-36 or NPY 3-36 in the test sample is free NPY 1-36 or free NPY 3-36.

Selected Kits

This invention also provides kits for conveniently and effectively assessing the amount of NPY 1-36 or NPY 3-36 in a sample. In certain embodiments, the kits may further comprise, or further consist essentially of, a molecular weight standard. In certain embodiments, the pure standard(s) may be a commercially available standard. In a specific embodiment, the internal standard is deuterated NPY 1-36. In another specific embodiment, the internal standard is deuterated NPY 3-36. In certain embodiments, the kits may further comprise an additive. In certain embodiments, the additive is a protease inhibitor, a peptidase inhibitor, or an anti-oxidant (e.g., DTT).

A kit of the invention may include instructions in any form that are provided in connection with the methods of the invention in such a manner that one of ordinary skill in the art would recognize that the instructions are to be associated with the methods of the invention. For instance, the instructions may relate to the use, modification, mixing, diluting, and/or preparation of the sample. In some cases, the instructions may also include instructions for the use of the mass spectrometer. The instructions may be provided in any form recognizable by a user as a suitable vehicle for containing such instructions; for example, written or published, verbal, audible (e.g., telephonic), digital, optical, visual (e.g., videotape, DVD, etc.) or electronic communications (including Internet or web-based communications), provided in any manner.

EXEMPLIFICATION

The invention now being generally described, it will be more readily understood by reference to the following, which is included merely for purposes of illustration of certain aspects and embodiments of the present invention, and is not intended to limit the invention.

Example 1

Peptides, Chemicals, and Isotopic Peptides

NPY 1-36 and NPY 3-36 may be purchased at American Peptide Company (Sunnyvale, Calif.).

Peptides may be synthesized with an Applied Biosystems 433 apparatus (Foster City, Calif.), using Fmoc-protected amino acids of the highest purity commercially available from Novabiochem (Darmstadt, Germany) or Advanced Chemtech (Louisville, Ky.). (15%-$^{13}$C, 95%-$^{15}$N)-labeled N labeled amino acid may be provided by Senn Chemicals (Dielsdorf, Switzerland) and may be used to label NPY at positions 3, 5, 8, 13, 19, 22, 24, 30, 33, and 35, for example. The peptides may then be purified by reversed-phase HPLC with a Vydac $C_{18}$ column (Vydac, Deerfield, Ill.), (10×250 mm; flow rate: 3 mL×min$^{-1}$, linear gradient: 10% B to 50% B in 5 min, then 50% to 58% B in 29 min, A: 0.1% trifluoroacetic acid, B: 60% $CH_3CN$, 0.06% trifluoroacetic acid).

Example 2

Quantitative Analysis of Free NPY 1-36 and Free NPY 3-36 in a Sample by LC-MS QTOF Sample Preparation: 600 μL of the sample were centrifuged using a Centrifree YM 30 (Millipore) at 2500 rpm (37° C.) for 30 minutes. Then, 100 μL of standard, quality control or sample (ultrafiltrate) were mixed with 150 μL of deuterated neuropeptide Y 1-36 in methanol. The mixture was vortexed for 30 sec, centrifuged at 13,000 rpm for 10 min. The clear supernatant was diluted with equal amount of water.

LC-MS QTOF: 100 μL of the sample was injected onto a LC-MS QTOF.

HPLC Conditions—HPLC=Agilent HPLC 1200 Series; Column=Zorbax SB-C18 Rapid Resolution HT Cartridge Column (Agilent part no. 821700-902); Solvent A=0.1% formic acid in 2% methanol (v/v); Solvent B=0.1% formic acid in 99.9% methanol (v/v); injection volume=100 μL.

QTOF Conditions—QTOF=Agilent QTOF 6530; Ionization Mode=ESI-MS in positive; MS ions followed=NPY 1-36 (855.22480 (5$^+$)), NPY 3-36 (803.20380 (5$^+$)), D$^8$ NPY 1-36 (857.03450 (5$^+$)); Ionization Source=ESI; Ionization Mode=Positive; Gas Temperature:=300° C.; Drying Gas=2; Nebulizer=45 psig; Sheath Gas Temperature=250° C.; Sheath Gas Flow=7 L/min; VCAP=3000 V; Fragmentor=200 V; Skimmer=65 V; Nozzle Voltage=500 V.

Figure 8:
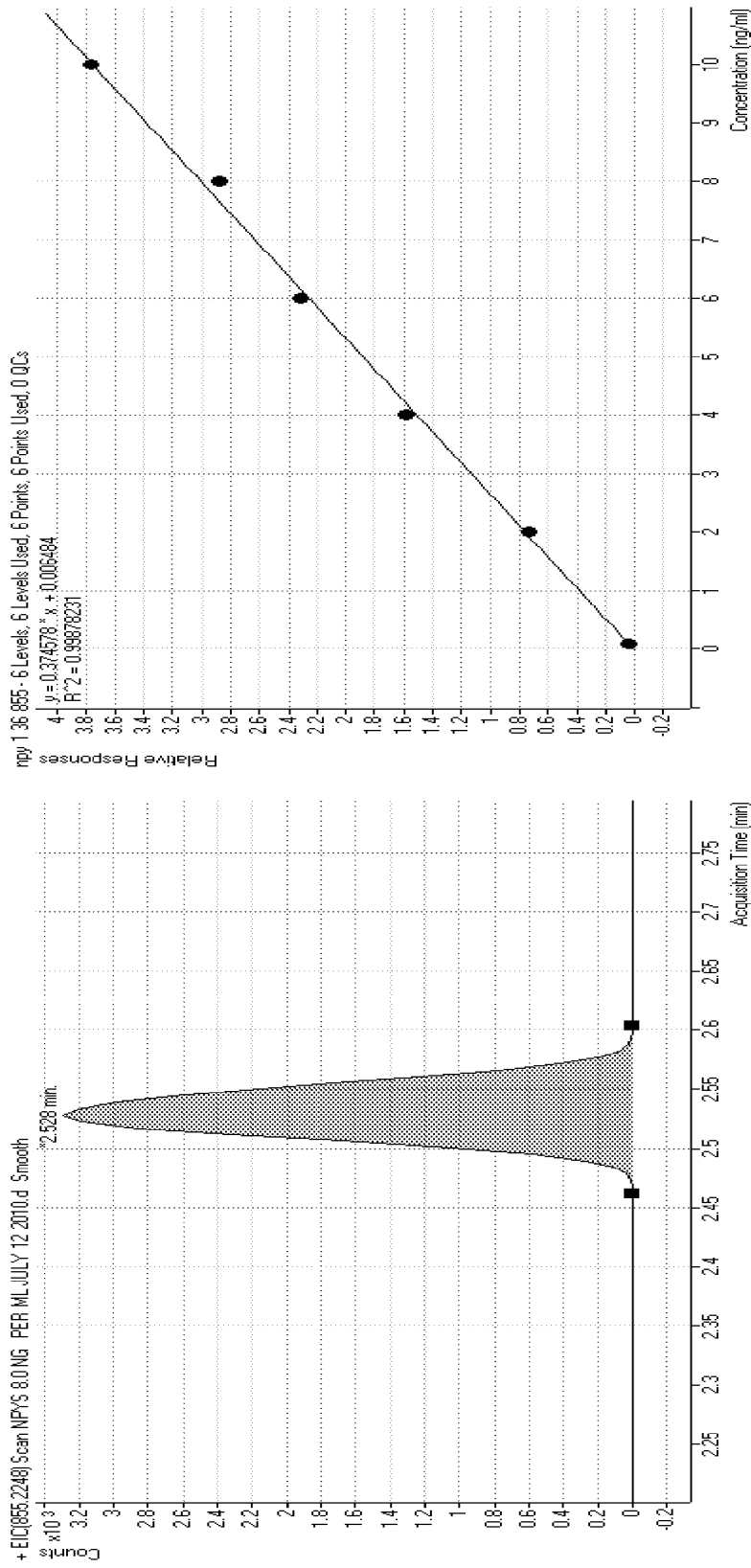
FIG. 8 depicts a NPY 1-36 standard curve and chromatogram. These data were obtained via TOF using accurate mass.
Figure 9:
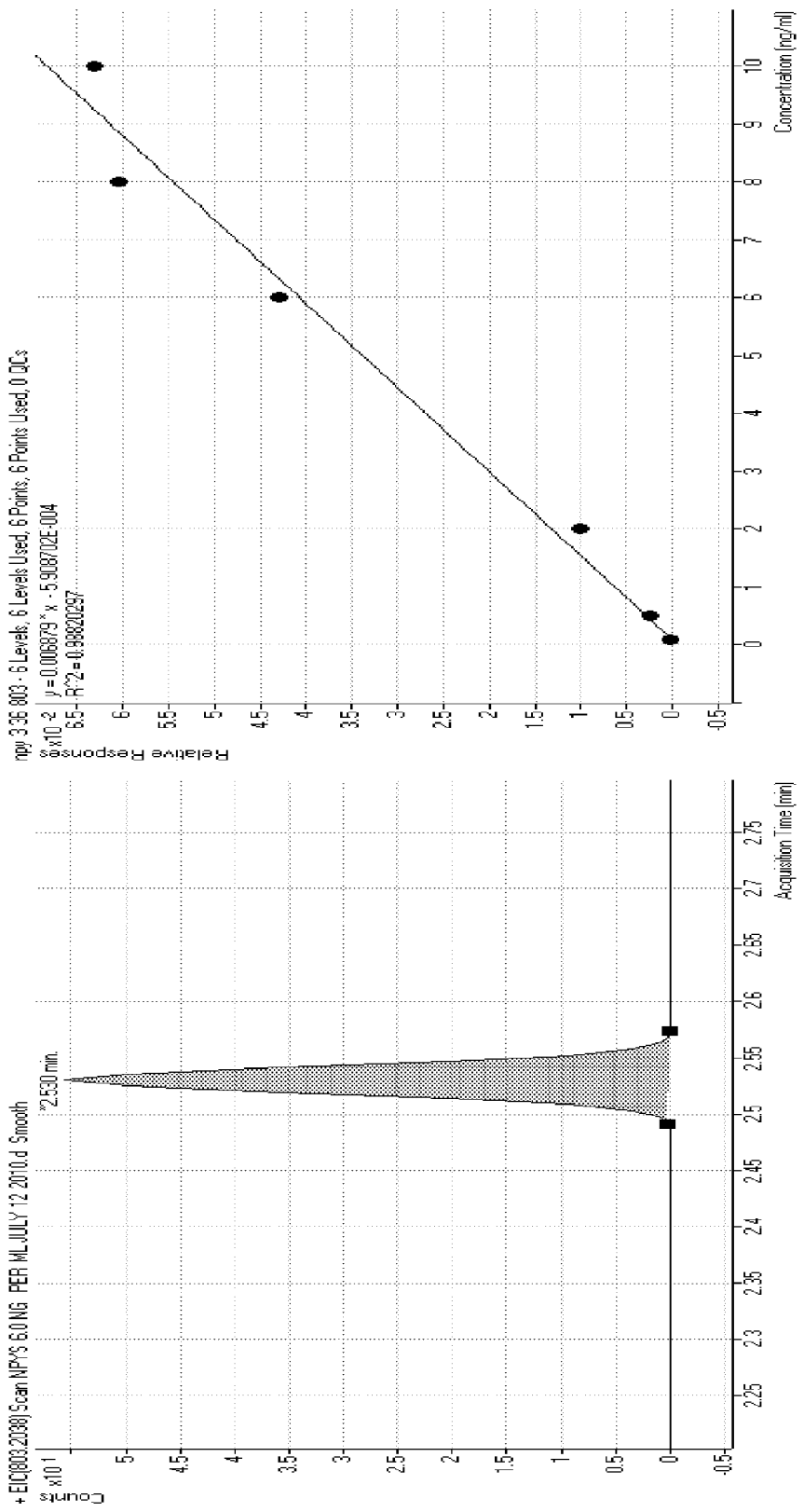
FIG. 9 depicts a NPY 3-36 standard curve and chromatogram. These data were obtained via TOF using accurate mass.

FIG. 8 depicts a NPY 1-36 standard curve and chromatogram. FIG. 9 depicts a NPY 3-36 standard curve and chromatogram.

Example 3

Quantitative Analysis of Free NPY 1-36 and Free NPY 3-36 in a Sample by MS/MS

Sample preparation: Sample was subjected to ultra filtration at 37° C. for 30 minutes; 200 μL of filtrate were added to 300 μL of working internal standard in methanol; the mixture was centrifuged for 10 minutes at 13000 rpm; 400 μL of supernatant were added to 800 of DI water; calibrators were prepared in DI water; 650 μL were injected.

MSMS: API 5000 Positive ESI source; Shimadzu LC; Loading sample=20% Methanol in DI adjust pH to 4.0 with acetic acid; Elute sample=Mobile Phase A: 0.1% TFA in water, Mobile Phase B: 0.1% TFA in methanol; Column=Phenomenex Jupiter C18 50 mm×2.0, 3 micron; Flow=0.4 mL/min; Gradient=Elute for 3 min with 55% B and go up to 90% B between 3-5 min, wash the column with 100% B then equilibrate the column to the initial conditions.

Figure 10:
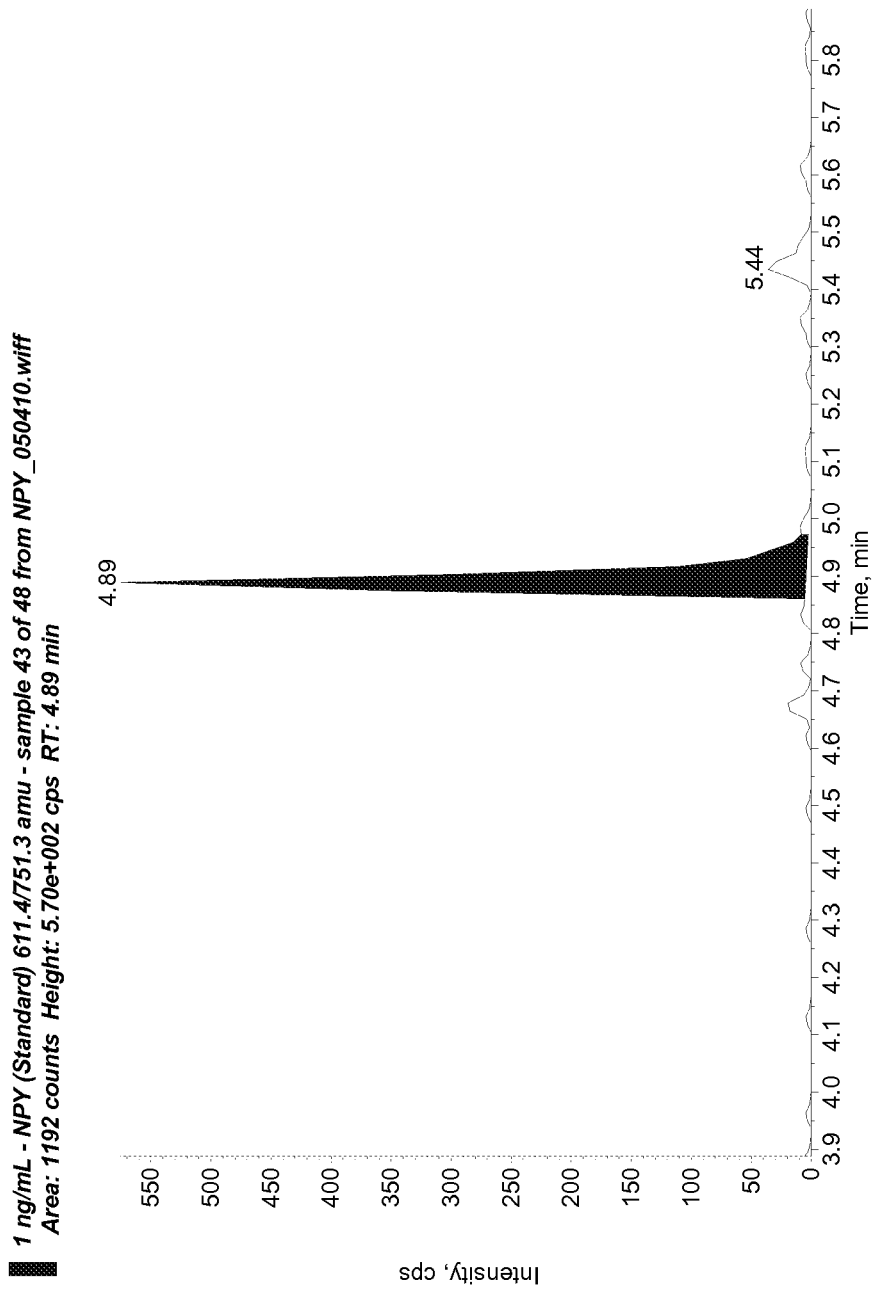
FIG. 10 depicts a chromatogram of 1 ng/mL of $[NPY\ 1\text{-}36]^{7+}$ from m/z 611.4 to 751.3. These data were obtained via ESI tandem MS/MS using multiple reaction monitoring (MRM) on an API 5000 LC/MS/MS.
Figure 11:
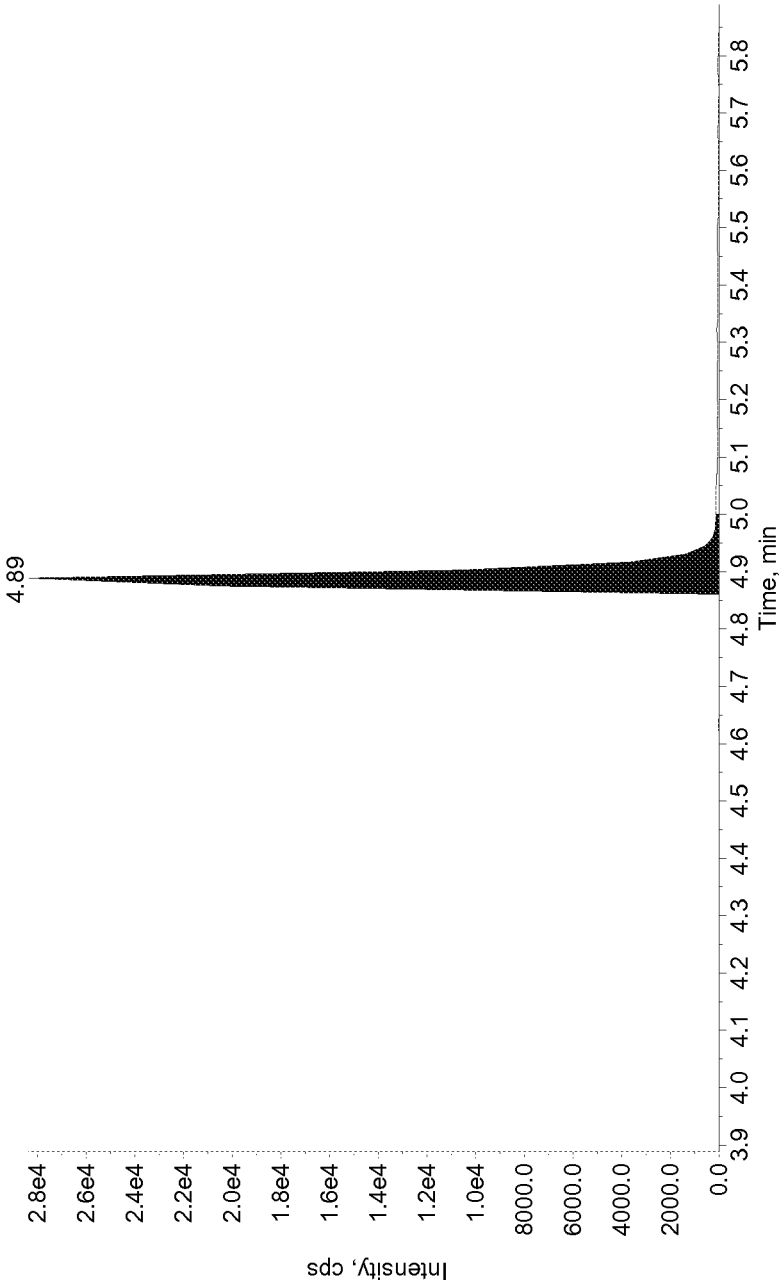
FIG. 11 depicts a chromatogram of 1 ng/mL $D_8$-NPY 3-36 used as a reference peptide, or internal standard, from m/z 575.3 to 603.0. These data were obtained via ESI tandem MS/MS using MRM on an API 5000 LC/MS/MS.
Figure 12:
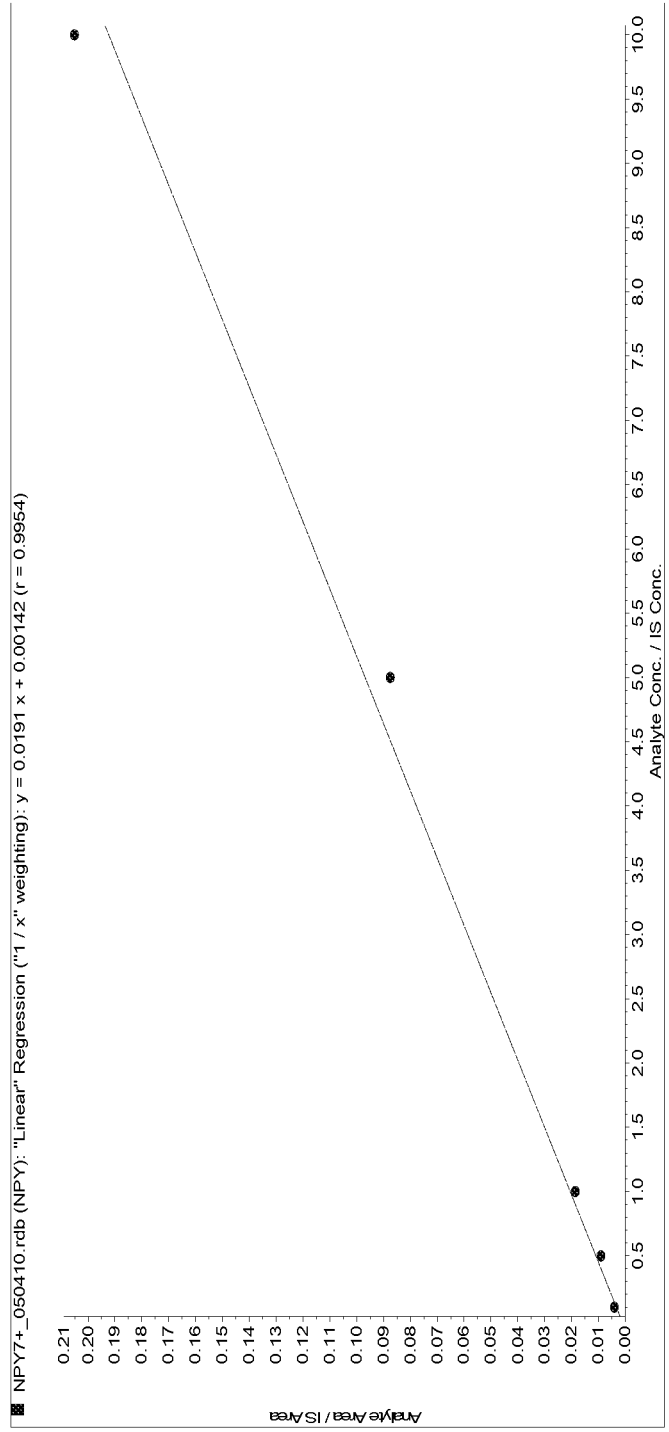
FIG. 12 depicts a tandem MS/MS calibration curve for $[NPY\ 1\text{-}36]^{7+}$ from 0.1 ng/mL to 10 ng/mL.
Figure 13:
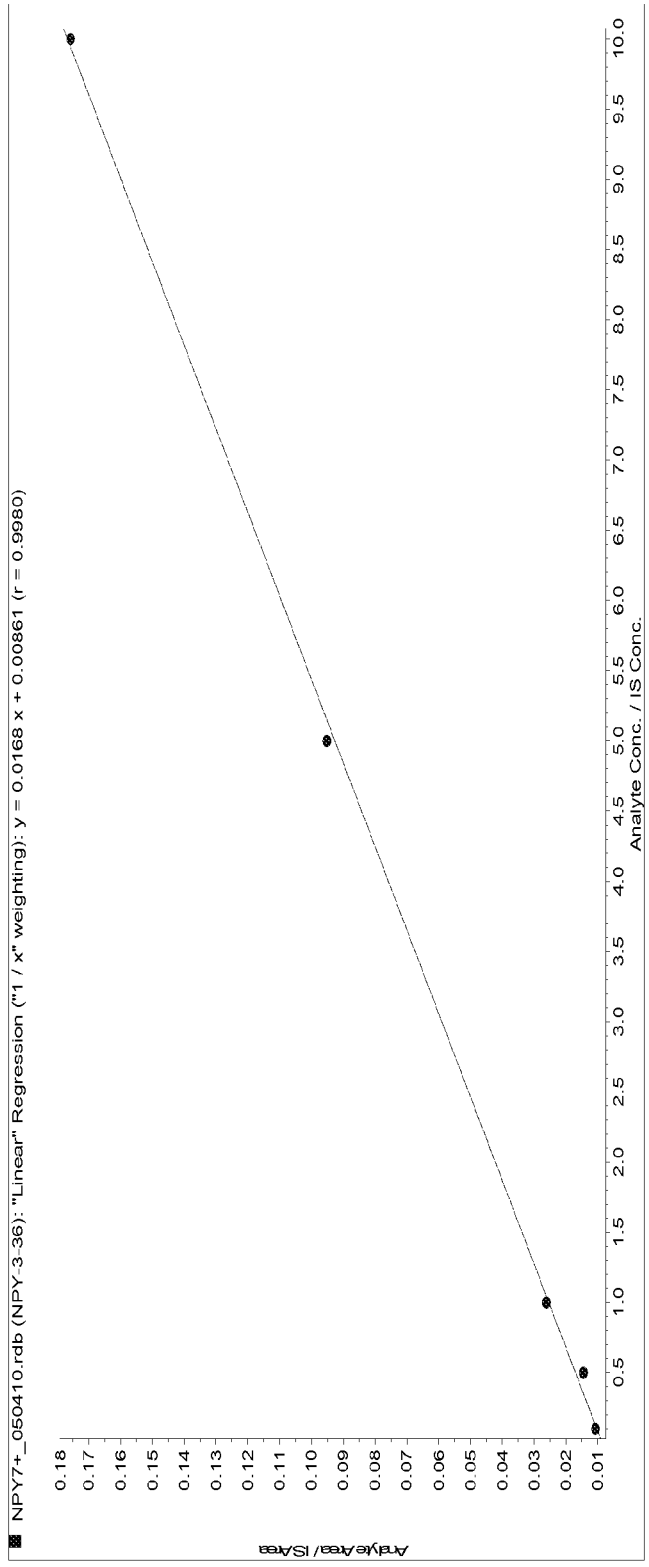
FIG. 13 depicts a tandem MS/MS calibration curve for $[NPY\ 3\text{-}36]^{7+}$ from 0.1 ng/mL to 10 ng/mL.

FIG. 10 depicts a chromatogram of 1 ng/mL of [NPY 1-36]$^{7+}$ from m/z 611.4 to 751.3. FIG. 11 depicts a chromatogram of 1 ng/mL $D_8$-NPY 3-36 used as a reference peptide, or internal standard, from m/z 575.3 to 603.0. FIG. 12 depicts a calibration curve for [NPY 1-36]$^{7+}$ from 0.1 ng/mL to 10 ng/mL. FIG. 13 depicts a calibration curve for [NPY 3-36]$^{7+}$ from 0.1 ng/mL to 10 ng/mL.

Example 4

Quantitative LC-MS$^n$ Analysis of NPY Fragments

The LC-MS$^n$ system can consist of a Rheos Allegro UHPLC pump (Flux Instruments, Basel, Switzerland), an HTC PAL autosampler (CTC Analytics AG, Zwingen, Switzerland) and a linear ion trap mass spectrometer (LTQ-MS) from ThermoFisher performing with an electrospray ion source in positive mode (ESI+). The analytical column may be a Hypersil Gold, 50-mm length, 1-mm inner diameter, 1.9 µm particle size (Thermo-Fisher). The mobile phase may be composed of phase A: 10 mM ammonium formate (Sigma) with 0.1% formic acid (Merck) in deionized water and phase B: 0.1% formic acid in acetonitrile (JT Baker). The mobile phase may be delivered at a flow rate of 0.15 mL/min with the following stepwise gradient: 10% of B at 0 min, 90% of B at 2 min, 100% of B at 3.5 min for 4.5 min, and back to 10% of B at 8 min for 4 min. The total run time may be 12 min. The injection volume may be 10 µL.

For the LTQ-MS ion source, the sheath and auxiliary gas (nitrogen) flow-rate may be set at 40 psi and 10 arbitrary units, respectively, the capillary voltage may be +4 kV, the heated capillary temperature may be set at 250° C., and the tube lens voltages may range from 210 V to 250 V. LTQ-MS was operating in product ion scan mode acquisition. Each NPY and IS-NPY parent ions may be isolated in the LTQ-MS with an isolation width of 5 arbitrary units before their collision-induced dissociation and the generation of $MS^2$ product ions. In the trap, $He^2$ gas may be set at pressure at 275 kPa, and a collision energy of 25% may be chosen and may corresponded to the maximum abundance for the total ion current of the NPY product spectra. The maximum injection time may be set at 10 ms. Pure standards of NPY forms may be oxidized and tuned on the LTQ-MS to determine their parent and product ions. The following ion transitions may be chosen with the isolation of $[M+3H]^{3+}$ parent ions:

NPY 1-36: m/z at 1430.23; extracted product ion chromatogram (EIC) at m/z 1200.5/1343.6/1397.06/1402.9/1408.0/1409.0/1410.0/1412.2/1544.4/1545.4.

NPY 3-36: m/z at 1343.53, EIC at m/z 1200.5/1315.5/1316.5/1321.8/1322.65/1330.5/1535.9/1543.9.

Example 5

Preparation of Calibration Curves

Figure 5:
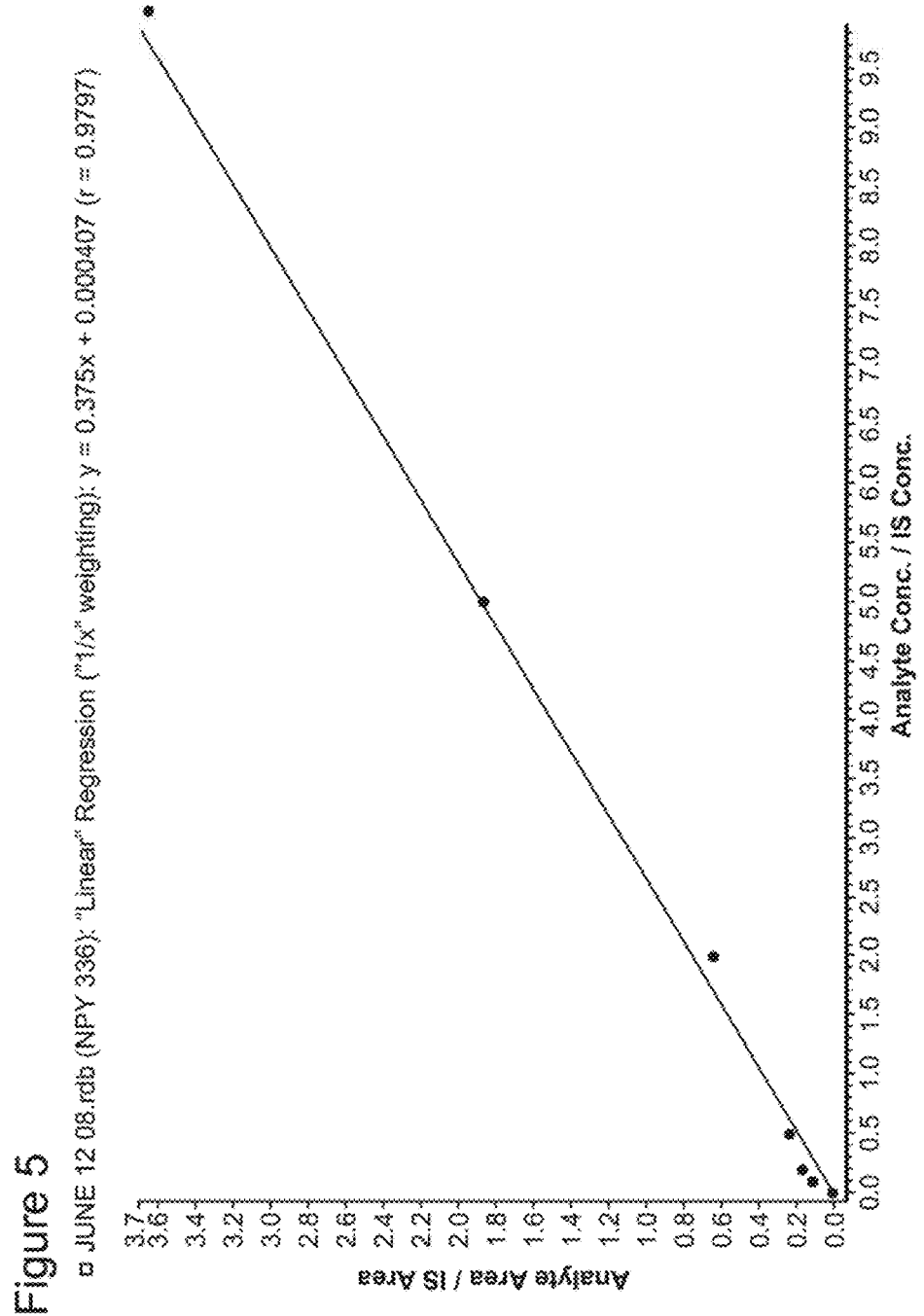
FIG. 5 depicts the calibration curve generated by samples 1 through 7 from FIG. 4. The curve displays a linear relationship up to a concentration of about 10 ng/mL of NPY 3-36.
Figure 6:
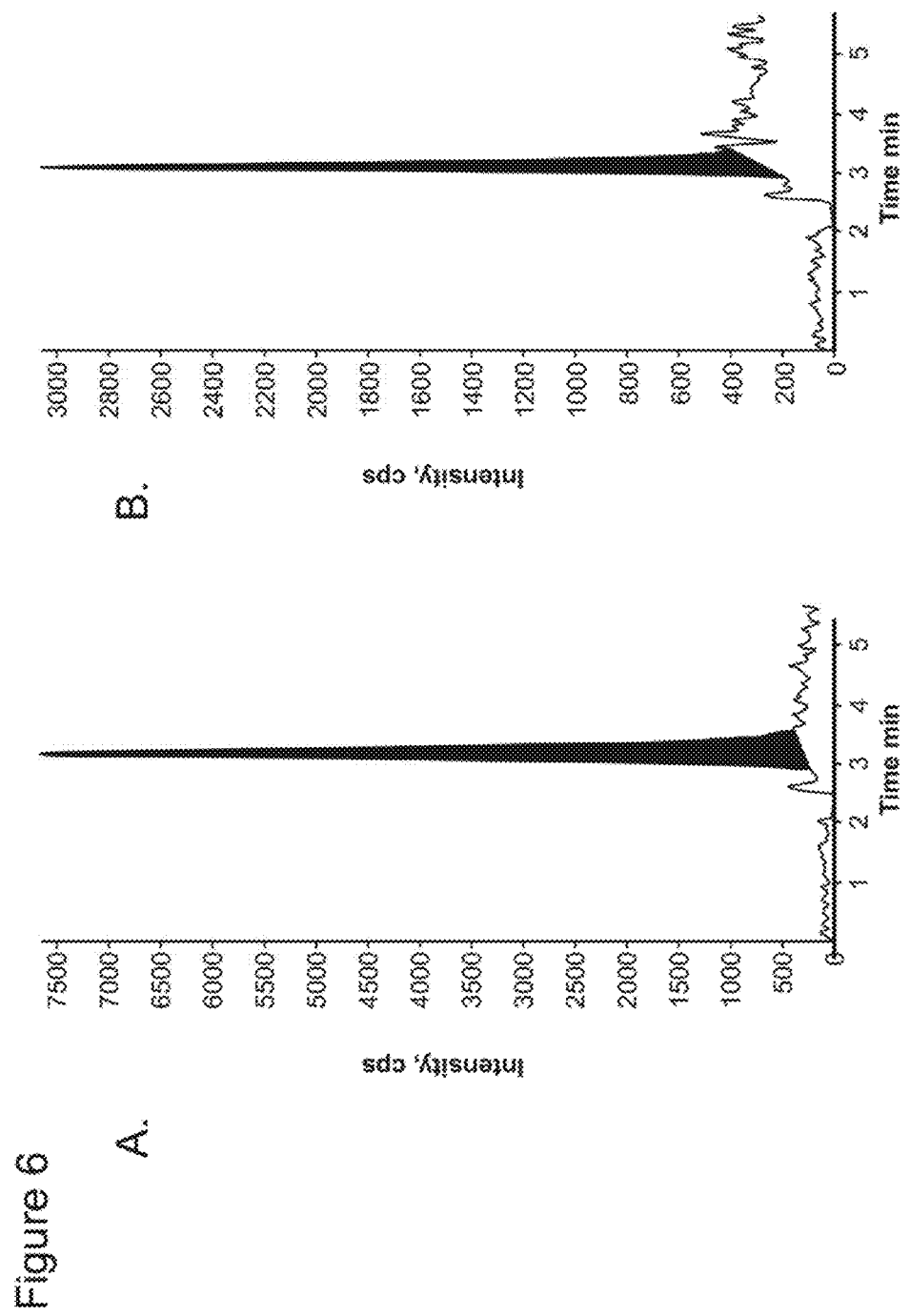
FIG. 6 depicts NPY 3-36 chromatograms, as produced on an API 4000 LC/MS/MS.
Figure 7:
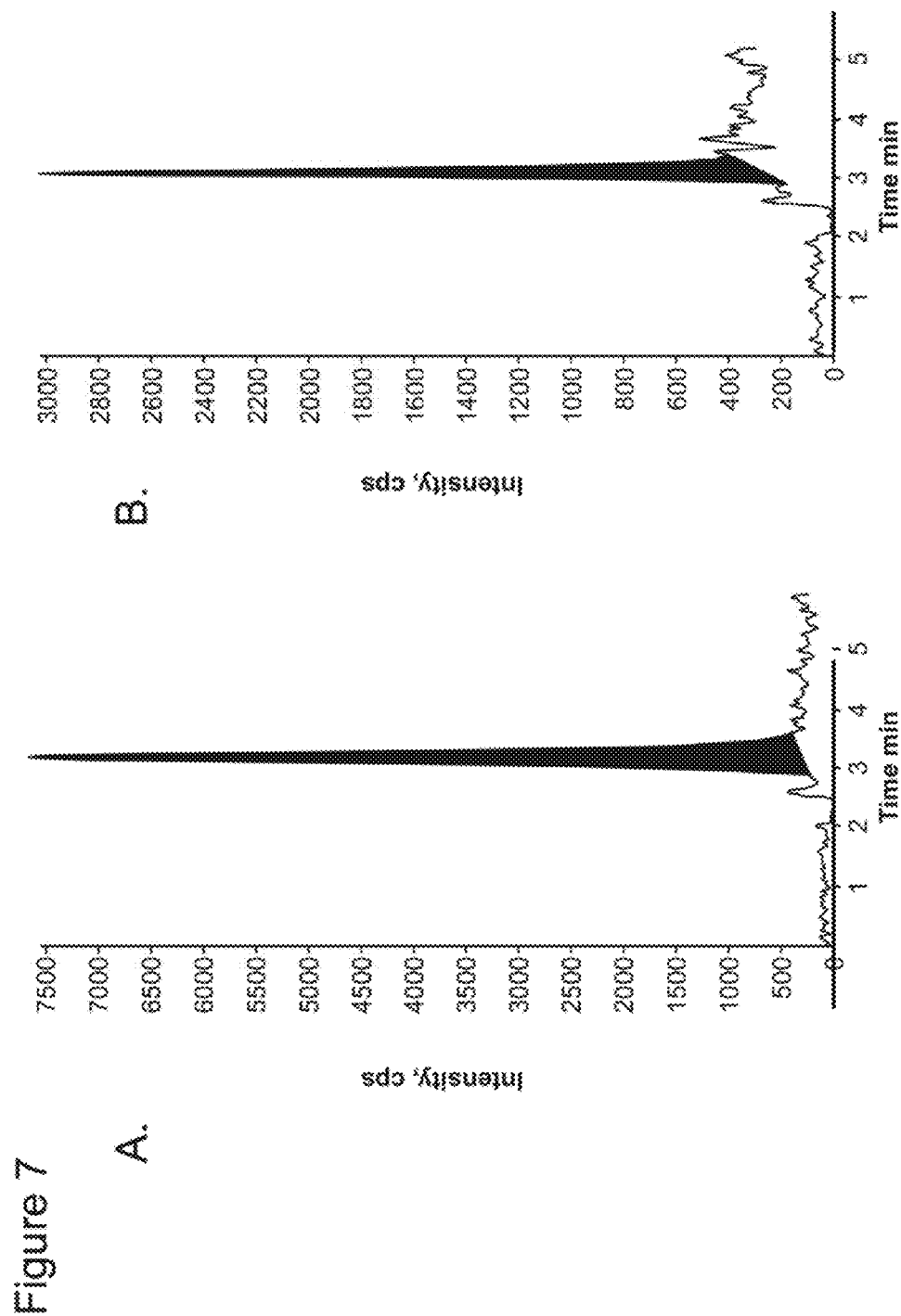
FIG. 7 depicts NPY 3-36 chromatograms, as produced on an API 4000 LC/MS/MS.

A calibration curve for NPY 1-36 is shown in FIG. 2. A calibration curve for NPY 3-36 is shown in FIG. 5. These data were obtained on an API 4000 LC/MS/MS.

Example 6

Quantitative Analysis Using HPLC-QTOF-MS

A HPLC-QTOF-MS system (1200 Series connected to an 6530 QTOF mass spectrometer, Agilent Technologies, Santa Clara, Calif.) equipped with a reverse phase C18 column [2.1×15 mm and 1.8 µm particle size (Zorbax SB-C18)] was used. Column temperature was maintained at 50° C. Mobile phases A and B were 2% methanol and 100% methanol both containing 0.2% formic acid. The Jetstream ESI interface was operated in the positive mode, using the parameters: capillary voltage 3000 V; nebulizer pressure 35 psig; drying gas 9 L $min^{-1}$; gas temperature 370° C.; fragmentation voltage 200 V; skimmer voltage 65 V; octopole RF 750 V. LC/MS accurate mass spectra were recorded across the range 100-1700 m/z. The TOF was calibrated on a daily basis and subsequently operated at high accuracy (<5 ppm) without utilizing reference masses. Data were collected in centroid mode at a rate of 1 spectrum per s in the extended dynamic range mode (2 GHz). All data were acquired using MassHunter software (Agilent Technologies).

900 µL of human plasma containing 10 mM of DTT was placed in a Centrifree YM-30 ultrafiltration device (30,000 MW cut-off, Millipore), and centrifuged at 2700 rpm for 30 min at 37° C. 30 µL of formic acid (10%) and 40 µL of 100 mM DTT were added to 400 µL of the ultrafiltrate. The latter was deproteinized with 700 µL of methanol containing deuterated internal standards. The resulting sample was centrifuged at 10,000 rpm for 5 minutes and 900 µL were loaded onto the LC column.

NPY 1-36 and 3-36 peptide fragments were quantified in MS mode only. The ions chosen for quantification were 803.20380 for NPY 3-36($d_4$-805.240810), 855.22480 for NPY 1-36 ($d_2$-857.03450).

After sample injection the column was washed with 20% methanol for 6 minutes. All wash and gradient solutions contained 0.2% formic acid. The methanol gradient for the period 6.1 to 9.0 minutes was 20-90%, for 9.1-10 minutes 90-100% and for the period 10-13 minutes 100% methanol. The retention times for NPY 1-36, 3-36 and deuterated ISs were between 11.527 and 11.539 minutes.

The LOQ for the NPYs were 0.1 ng/mL. The recoveries were >90% for both peptides. Linearity was good between 0.1-2 ng/mL. CVs <10% between 0.2-2 ng/mL. Preliminary data indicate values for healthy normals are in the range of 0.23-0.67 ng/mL (NPY 1-36) and 0.19-0.65 ng/mL (NPY 3-36).

Example 7

Quantitative Analysis Using HPLC-QTOF-MS 0.9 mL of human plasma containing 10 mM of DTT is placed in a Centrifree YM-30 ultrafiltration device (30,000 MW cut-off, Millipore), and centrifuged at 2,700 rpm for 30 min at 37° C. 30 µL of formic acid (10%) and 40 µL of 100 mM DTT were added to 400 µL of the ultrafiltrate. The latter was deproteinized with 700 µL of methanol containing deuterated internal standards. 0.9 mL was then loaded onto the LC column.

Gradient Profile: After sample injection the column was washed with 20% methanol for 6 minutes. All wash and gradient solutions contained 0.2% formic acid. The methanol gradient for the period 6.1 to 9.0 minutes was 20-90%, for 9.1-10.0 minutes 90-100% and for the period 10.0-13.0 minutes 100% methanol. The retention times for NPY 1-36, NPY 3-36 and deuterated internal standards were between 10.025 and 10.037 minutes.

HPLC Column: A reverse phase C18 column [2.1×15 mm and 1.8 µm particle size (Zorbax SB-C18)]. Column temperature was maintained at 50° C.

Preliminary data indicate reference intervals for healthy normal subjects range from 0.23-0.67 ng/mL for NPY 1-36, and 0.19-0.65 ng/mL for NPY 3-36.

Figure 16:
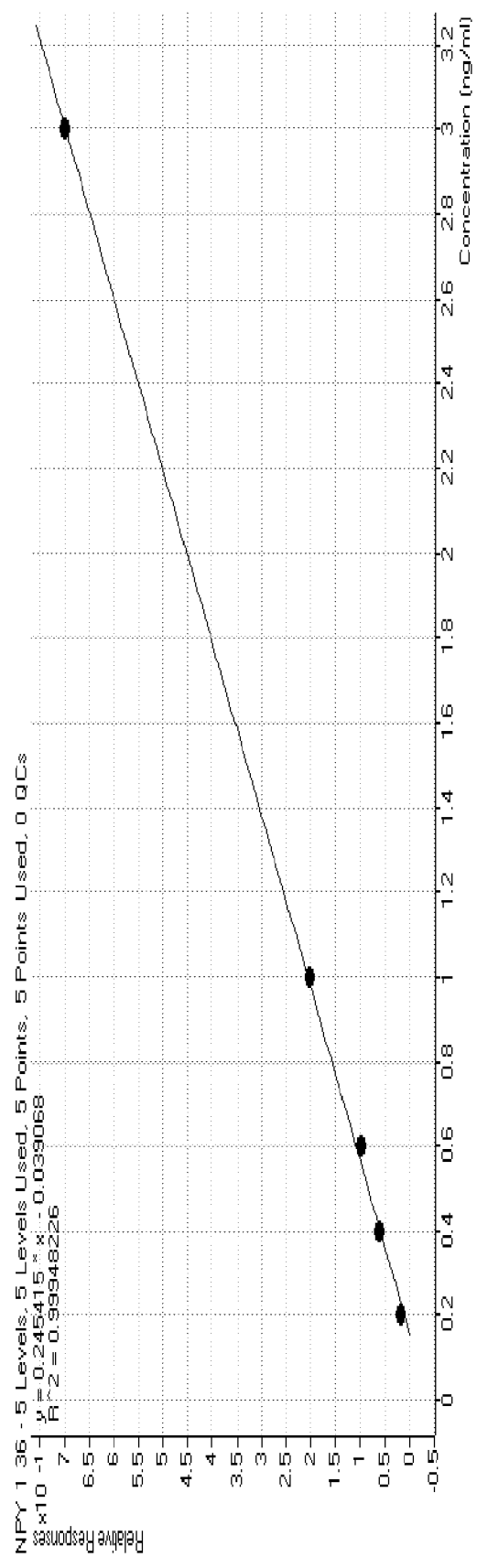
FIG. 16 depicts a calibration curve for NPY 1-36 from 0.2 ng/mL to 3 ng/mL.
Figure 17:
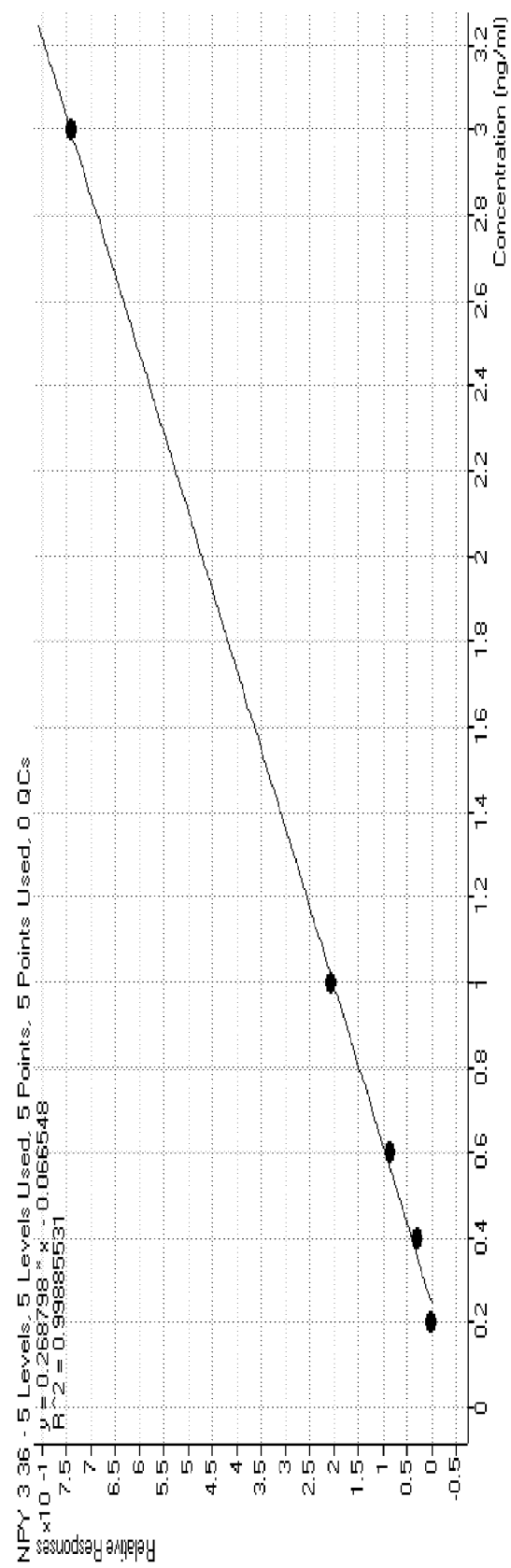
FIG. 17 depicts a calibration curve for NPY 3-36 from 0.2 ng/mL to 3 ng/mL.
Figure 18:
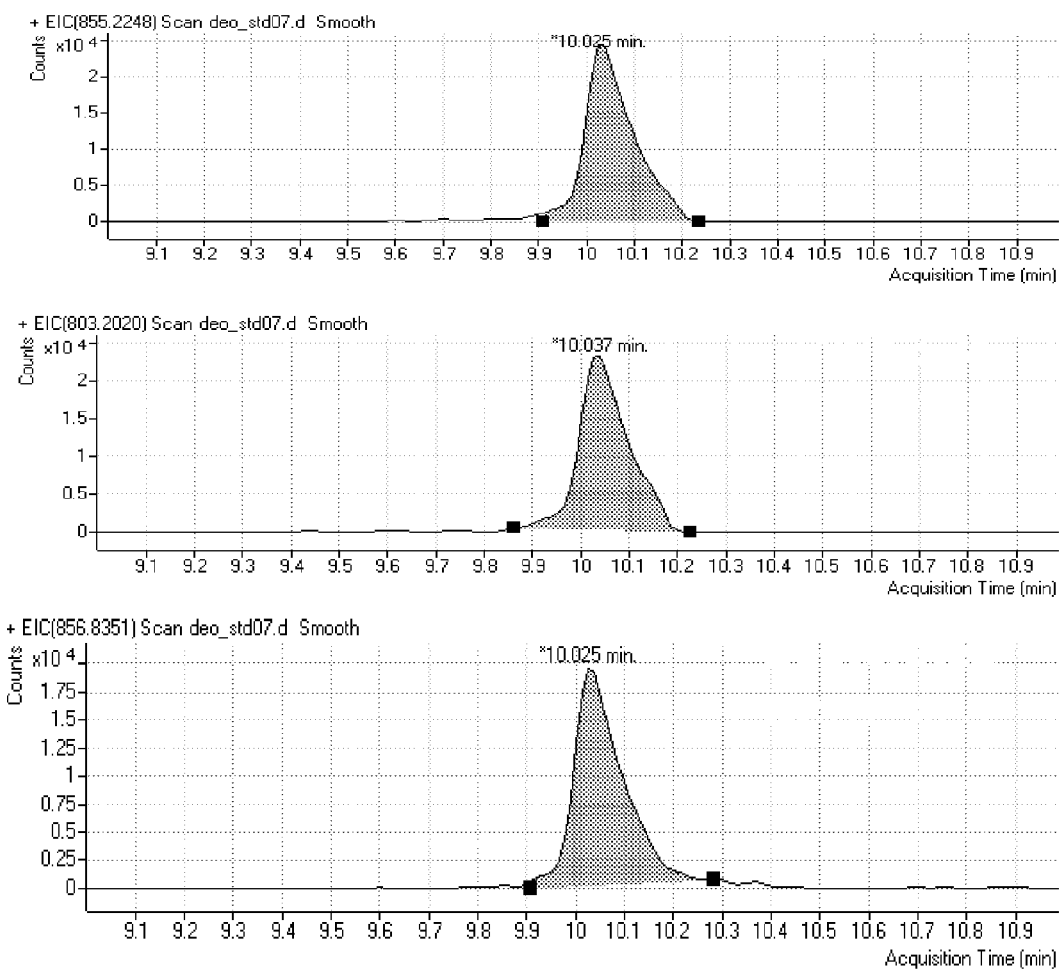
FIG. 18 depicts a chromatogram of NPY 1-36 (top), NPY 3-36 (middle), and deuterated NPY 1-36 (bottom).

See FIGS. 16, 17, and 18.

Example 8

Exemplary Experimental Details

NPY

Analytical column (cartridge): Agilent Zorbax Eclipse XDB-C18, 1.8 u 15×2.1 mm, P#921700-932 or Agilent Zorbax SB-C 18.

Figure 15:
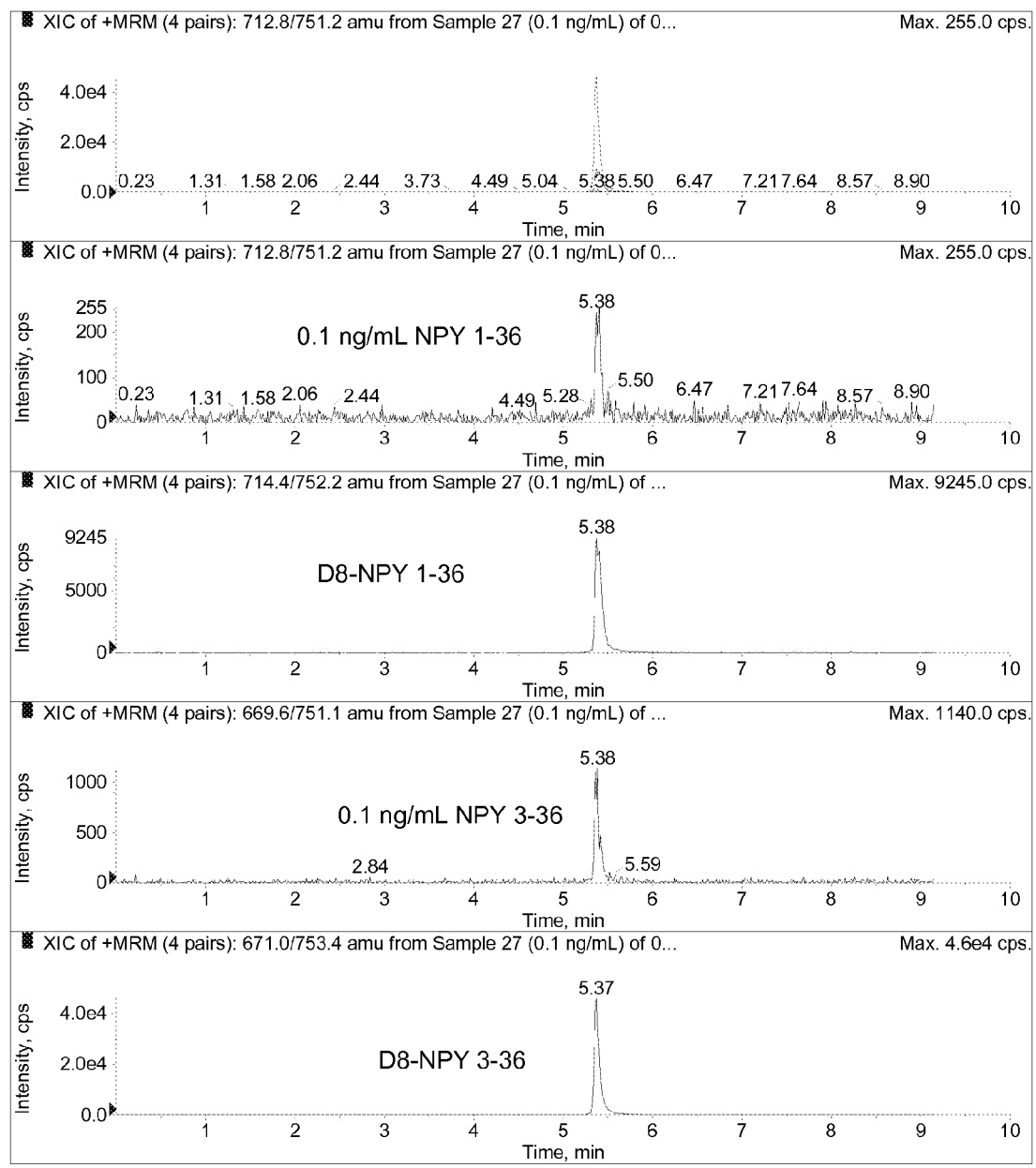
FIG. 15 depicts a series of chromatograms, as produced on an API 5000 LC/MS/MS triple quadrupole MS.

Pump A: 0.2% Formic acid in DI water
    Pump B: 0.2% Formic acid in Acetonitrile
    Pump C: 0.2% Formic acid in 98/2 DI/Methanol
    Pumps A & B for elution
    Pump C for loading
Load: Pump C 0.4 mL/minute on column for 4 minutes Elute: Pump A and B 0.35 mL/min from 15% B to 72% B in 3 minutes. (Forward flush the column)
Clean the column with 100% B for 1.5 minute; then 5% B for 1 minute; re-equilibrate the column with pump C for 0.2 minute before each injection.
The acquisition method is depicted in FIG. 14 (NPY Agilent C18).
Sample Prep: (for calibrators in 0.1% FA/methanol)
200 mcL of calibrators in 0.1% FA in methanol in micro centrifuge tube
Add 10 mcL of ISTD (0.1 ng/mcL) in methanol
Add 100 mcL of 5 mM Dithio-DL-threitol in DI water
100 mcL of 1% FA in water
100 mcL DI water
100 mcL of 0.1% FA in methanol
Vortex and centrifuge for 10 minutes @ 13000 RPM
Transfer to vials
Inject 400 mcL
Sample Prep: (for serum samples)
500 mcL of serum in plastic test tube
Equilibrate at 37° C. for 30 minutes
Transfer to an ultrafiltration device (add 20 mcL of 20 mMol DDT in collection tube), centrifuge for 40 minutes at 2800 RPM at 37° C.
200 mcL of ultrafiltrated sample
10 mcL of Istd
100 mcL of 1% FA in water
300 mcL of 0.1% FA in methanol
Vortex and centrifuge for 10 minutes @13000 RPM
Transfer to autosampler vial. It's ready for injection. See FIG. 15.

| | |
|---|---|
| NPY 1-36 | 712.8→751.2 |
| NPY 1-36-D8 ISTD | 714.4→752.2 |
| NPY 3-36 | 669.6→751.1 |
| NPY 3-36-D8 ISTD | 671→753.4 |

Example 9

Comparison of Release of NPY by Tumor Cells

Conditioned media collected after 24 h culture were subjected to ultrafiltration at 37° C. and 2900 rpm using 30 Kd cutoff filters. The ultrafiltrate contained around 7 mg/dL protein plus peptides which include NPY 1-36 and NPY 3-36. These were then quantified using multiple reaction mode monitoring (MRM). The MRM for NPY 1-36 was 1068.8/70.1 and for NPY 3-36 was 803.4/70.1 on the API-4000 Tandem Mass Spectrometer (AB Sciex, Foster City, Calif.). Deuterated NPY 1-36 was used as internal standard (MRM 857.1/70.1).

ESFT cell lines not responsive to NPY release high levels of NPY 3-36. The forms of NPY released by ESFT (Ewing's sarcoma family of tumors) cells in responsive and non-responsive cells were compared by MS. In SK-N-MC (human ESFT cell line) conditioned media, NPY was detected mostly in its intact form, NPY 1-36. In contrast, approximately 50% of NPY released by SK-ES cells (ESFT cells not responsive to NPY release) was in its cleaved form, NPY 3-36, inactive at Y1Rs. The relevance of these findings was confirmed by the fact that in SK-N-MC cells, the decrease in cell viability was achieved with NPY 1-36, but not with NPY 3-36. Since NPY 3-36 is a product of DPPIV cleavage, the above results suggested that the lack of the responsiveness to NPY in some ESFT cells might result from elevated DPPIV-like activity.

See Lu, C., et al. "Dipeptidyl Peptidases as Survival Factors in Ewing's Sarcoma Family of Tumors—Implications for Tumor Biology and Therapy." *J. Biol. Chem.* 2011, 286: 27494-27505, hereby incorporated by reference.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

I claim:

1. A method of assaying for NPY 1-36 and a fragment of NPY 1-36, which method comprises:
   a) preparing a test sample, wherein the test sample comprises NPY 1-36 and a fragment of NPY 1-36;
   b) combining the test sample with a known quantity of a first reference peptide for the NPY 1-36 and a second reference peptide for the fragment of NPY 1-36, thereby forming a test sample comprising an internal standard for each of the NPY 1-36 and the fragment of NPY 1-36; and
   c) determining by mass spectrometry the quantity of the NPY 1-36 and the fragment of NPY 1-36 in the test sample and the quantity of each of the first and second reference peptides in the test sample, and calibrating the quantity of the NPY 1-36 against the known and determined quantities of the first reference peptide in the test sample and the quantity of the fragment of NPY 1-36 in the test sample against the known and determined quantities of the second reference peptide in the test sample, thereby determining the absolute quantity or absolute concentration of the NPY 1-36 and the fragment of NPY 1-36 in the test sample, wherein the first reference peptide is NPY 1-36, human NPY 1-36, porcine NPY 1-36, or isotopically labeled NPY 1-36; and the second reference peptide is isotopically labeled NPY 3-36.

2. The method of claim 1, wherein the first reference peptide is deuterated NPY 1-36; and the second reference peptide is deuterated NPY 3-36.

* * * * *